United States Patent
Gilbert et al.

(10) Patent No.: US 7,022,663 B2
(45) Date of Patent: Apr. 4, 2006

(54) ORAL, NASAL AND PULMONARY DOSAGE FORMULATIONS OF COPOLYMER 1

(75) Inventors: Adrian Gilbert, Kfar Sava (IL); Rivka Riven-Kreitman, Kfar Sava (IL); Milka Linenberg, Tel-Mond (IL); Sharon Cohen-Vered, Kfar Sava (IL); Ramon F. Joubran, Ramle (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 474 days.

(21) Appl. No.: 09/788,131

(22) Filed: Feb. 16, 2001

(65) Prior Publication Data

US 2001/0055568 A1 Dec. 27, 2001

Related U.S. Application Data

(60) Provisional application No. 60/183,666, filed on Feb. 18, 2000.

(51) Int. Cl.
 A61K 39/00 (2006.01)
 A61K 9/28 (2006.01)
 A61K 9/48 (2006.01)
 B05D 3/00 (2006.01)

(52) U.S. Cl. .................... 512/2; 424/452; 424/465; 424/474; 424/491; 424/494; 424/185.1; 427/2.16; 427/2.19; 427/2.21; 514/12

(58) Field of Classification Search .............. 514/2, 514/12; 424/452, 465, 474, 491, 494, 185.1; 427/2.16, 2.19, 2.21
See application file for complete search history.

(56) References Cited

U.S. PATENT DOCUMENTS

| | | | |
|---|---|---|---|
| 3,849,550 A | | 11/1974 | Teitelbaum et al. |
| 3,991,210 A | * | 11/1976 | Shea |
| 4,129,666 A | * | 12/1978 | Wizerkaniuk .............. 427/2.19 |
| 4,339,431 A | | 7/1982 | Gaffar |
| 5,075,115 A | * | 12/1991 | Brine ......................... 424/486 |
| 5,204,099 A | | 4/1993 | Barbier et al. |
| 5,554,372 A | | 9/1996 | Hunter et al. |
| 5,583,031 A | | 12/1996 | Stern |
| 5,591,629 A | | 1/1997 | Rodriguez et al. |
| 5,623,052 A | | 4/1997 | McLean et al. |
| 5,627,206 A | | 5/1997 | Hupe et al. |
| 5,668,117 A | | 9/1997 | Shapiro et al. |
| 5,719,296 A | | 2/1998 | Acton, III et al. |

(Continued)

FOREIGN PATENT DOCUMENTS

EP 0383620 8/1990

(Continued)

OTHER PUBLICATIONS

Kropshofer et al., "Self-Peptides from Four HLA-DR Alleles Share Hydrophobic Anchor Residues Near the $NH_2$-Terminal Including Proline as a Stop Signal for Trimming", *J. Immunol.*, 1993, 151:4732-4742.

(Continued)

*Primary Examiner*—Christina Chan
*Assistant Examiner*—F. Pierre VanderVegt
(74) *Attorney, Agent, or Firm*—John P. White, Esq.; Cooper & Dunham LLP

(57) ABSTRACT

Pharmaceutical compositions useful for treating autoimmune diseases in a mammal comprising as an active ingredient a therapeutically effective amount of Copolymer 1, and microcrystalline cellulose are disclosed. Processes for the manufacture of such compositions are also disclosed.

51 Claims, 6 Drawing Sheets

U.S. PATENT DOCUMENTS

| | | | |
|---|---|---|---|
| 5,734,023 A | 3/1998 | Nag et al. | |
| 5,800,808 A | 9/1998 | Konfino et al. | |
| 5,858,964 A | 1/1999 | Aharoni et al. | |
| 5,886,156 A | 3/1999 | McLean et al. | |
| 5,958,972 A | 9/1999 | Hupe et al. | |
| 5,965,600 A * | 10/1999 | Sato et al. | 514/419 |
| 5,981,589 A | 11/1999 | Konfino et al. | |
| 6,024,981 A * | 2/2000 | Khankari et al. | 424/464 |
| 6,048,898 A | 4/2000 | Konfino et al. | |
| 6,054,430 A | 4/2000 | Konfino et al. | |
| 6,162,800 A * | 12/2000 | Dolle et al. | 514/86 |
| 6,214,791 B1 | 4/2001 | Arnon et al. | |
| 6,342,476 B1 | 1/2002 | Konfino et al. | |
| 6,362,161 B1 | 3/2002 | Konfino et al. | |
| 6,514,938 B1 | 2/2003 | Gad et al. | |
| 6,800,285 B1 | 10/2004 | Rodriguez et al. | |
| 6,800,287 B1 | 10/2004 | Gad et al. | |
| 6,844,314 B1 | 1/2005 | Eisenbach-Schwartz et al. | |
| 2002/0037848 A1 | 3/2002 | Eisenbach-Schwartz et al. | |
| 2002/0055466 A1 | 5/2002 | Aharoni et al. | |
| 2002/0077278 A1 | 6/2002 | Yong et al. | |
| 2002/0107388 A1 | 8/2002 | Vandenbark | |
| 2002/0115103 A1 | 8/2002 | Gad et al. | |
| 2002/0182210 A1 | 12/2002 | Rodriguez et al. | |
| 2003/0004099 A1 | 1/2003 | Eisenbach-Schwartz et al. | |
| 2003/0170729 A1 | 9/2003 | Klinger | |
| 2004/0006022 A1 | 1/2004 | Strominger et al. | |
| 2004/0106554 A1 | 6/2004 | Konfino et al. | |
| 2005/0014694 A1 | 1/2005 | Yong et al. | |
| 2005/0019322 A1 | 1/2005 | Rodriguez et al. | |
| 2005/0038233 A1 | 2/2005 | Gad et al. | |

FOREIGN PATENT DOCUMENTS

| | | |
|---|---|---|
| EP | 0359783 | 11/1995 |
| WO | WO8810120 | 12/1988 |
| WO | WO9202543 | 2/1992 |
| WO | WO9403484 | 2/1994 |
| WO | WO9426774 | 11/1994 |
| WO | WO9526980 | 10/1995 |
| WO | WO9531990 | 11/1995 |
| WO | WO9531997 | 11/1995 |
| WO | WO9533475 | 12/1995 |
| WO | WO 98 30227 * | 7/1998 |
| WO | WO9830227 | 7/1998 |
| WO | WO0005249 | 2/2000 |
| WO | WO0005250 | 2/2000 |
| WO | WO0018794 | 4/2000 |
| WO | WO0020010 | 4/2000 |
| WO | WO0027417 | 5/2000 |
| WO | WO0152878 | 7/2001 |
| WO | WO0160392 | 8/2001 |
| WO | WO0185797 | 11/2001 |
| WO | WO0193828 | 12/2001 |
| WO | WO0193893 | 12/2001 |
| WO | WO0197846 | 12/2001 |
| WO | WO02076503 | 10/2002 |
| WO | WO03048735 | 6/2003 |

OTHER PUBLICATIONS

Henry, Celia M., "Special Delivery", *Chem. and Eng. News*, Sep. 18, 2000, 49-54.

Cohen, "Fundamental Immunology", *Systemic Autoimmunity*, 5th Ed., 1999, 1083.

Fridkis-Hareli et al., "Binding of random copolymers of three amino acids to class II MHC molecules", *Intl. Immunol.*, 1999, 11(5):633-641.

Li, et al., "Glatiramer acetate blocks the activation of THP-1 cells by interferon-y", *Eur. J. Pharmacol.*, 1998, 342: 303-310.

Zisman, et al., "Dichotomy between the T and the B cellepitopes of the synthetic polypeptide (T,G)-A--L", *Eur. J. Immunol.*, 1994, 24(10):2497-2505 (Abstract).

Deeb, et al., "Comparison of Freund's and Ribi adjuvants for inducing antibodies to the synthetic antigen (TG)-AL in rabbits", *J. Immunol. Methods*, 1992, 152(1): 105-113 (Abstract).

Zisman et al., "Direct Binding of a synthetic multichain polypeptide to class II Major Histocompatibility Complex Molecules on Antigen-Presenting Cells and stimulation of a specific T-cell line require processing of the polypeptide", *Proc. Natl. Acad. Sci. USA*, 1991, 88(21):9732-9742 (Abstract).

Matsunaga et al., "Complementation of class II A alleles in the immune response to (Glu-Lys-Tyr) polymers", *Yokohama Med. Bull.*, 1988, 39(1-2):9-19(Abstract).

De Kruyff et al., "Analysis of T Cell Responses to Poly-L (GluLys) at the Clonal Level. I. Presence of Responsive Clones in Nonresponder Mice", *Eur. J. Immunol.*, 1987, 17 (8): 1115-1120 (Abstract).

Lai et al., "Complementation of Class II A alleles in the immune response to (GluLysTyr) polymers", *Exp. Clin. Immuogenet.*, 1986, 3(1):38-48 (Abstract).

Lai, et al., "Monoclonal T cell responses to two epitopes on a single immunogen controlled by two distinct genes",*J. Immunol.*, 1986, 136(10):3799-3804 (Abstract).

Trannoy et al., "Epitope-specific regulation of the T cell repertoire: carrier recognition in association with I-E or I-A does not influence the restriction of hapten-specific T cells", *Eur. J. Immunol.*, 1985, 15(12):1215-1221 (Abstract).

Falo et al., "Analysis of antigen presentation by metabolically inactive accessory cells and their isolated membranes", *Proc. Natl. Acad. Sci. USA*, 1985, 82(19);6647-6651 (Abstract).

Babu et al., "Ir gene control of T and B Cell Responses to Determinants in (Glu Lys Ala) Terpolymer", *J. Immunogenet.*, 1984, 11(3-4): 251-254.

Babu et al., Reevaluation of response patterns of nonresponder mice to GLPhe polymers:, *Immunogen.*, 1983, 18(1):97-100 (Abstract).

Herzenberg et al., "Lack of immune response gene control for induction of epitope specific suppression by TGAL antigen", *Nature*, 1982, 295: 329-331 (Abstract).

Baxevanis et al., "Genetic Control of T-Cell Proliferative Responses to Poly $(Glu^{40}Ala^{60})$ and Poly $(Glu^{51}Lys^{34}Tyr^{15})$: Subregion-Specific Inhibition of the Responses with Monoclonal Ia Antibodies", *Immunogenetics*, 1980, 11: 617-628.

Maurer et al., "Interpretation of immune responses of mice to poly(Glu55Lys37Leu8) and the terpolymers poly (Glu55Lys37Leu8) and poly (Glu56Lys37Ser7)", *Clin. Immunol. Immunopathol.*, 1980, 15(3):34-356 (Abstract).

Ju et al., "Idiotypic analysis of antibodies against the terpolymer L-glutamic acid 60-L-alanine30-L-tyrosine10 (GAT). IV. Induction of CGAT idiotype following immunization with various synthetic polymers containing glutamic acid and tyrosine", *Eur. J. Immunol.*, 1979, 9(7): 553-560 (Abstract).

Schwartz et al., "Gene complementation in the T lymphocyte proliferative response to poly (Glu57Lys38Tyr5): Evidence for effects of polymer handling and gene dosage", *J. Immunol.*, 1979, 123(1):272-278 (Abstract).

Teitelbaum, et al., "Suppression of Experimental Allergic Encephalomyelitis by a Synthetic Polypeptide", *Eur. J. Immunol.*, 1971, 1, 242-248.

Teitelbaum, et al., "Suppression of Experimental Allergic Encephalomyelitis by a Synthetic Polypeptide", *Israel J. Med. Sci.*, 1971, 7, 630-631 (Abstract).

Arnon, et al., "Suppression of Experimental Allergic Encephalomyelitis by a Synthetic Copolymer Immunological Cross Reactive with Basic Encephalitogen", *Israel J. Med. Sci.*, 1972, 8, 1759-1760.

Teitelbaum, et al., "Protection Against Experimental Allergic Encephalomyelitis", *Nature*, 1972, 240, 564-566.

Webb, et al., "Further Studies on the Suppression of Experimental Allergic Encephalomyelitis by Synthetic Copolymer", *Israel J. Med. Sci.*, 1972, 8, 656-657.

Teitelbaum, et al., "Suppression of Experimental Allergic Encephalomyelitis with Basic Polymers", *Eur. J. Immunol.*, 1973, 3, 273-279.

Webb, et al., "In Vivo and in Vitro Immunological Cross-reactions between Basic Encephalitogen and Synthetic Basic Polypeptides Capable of Suppressing Experimental Allergic Encephalomyelitis", *Eur. J. Immunol.*, 1973, 3, 279-286.

Teitelbaum, et al., "Dose-response Studies on Experimental Allergic Encephalomyelitis Suppression by COP-1", *Israel J. Med. Sci.*, 1974, 10(9), 1172-1173.

Teitelbaum, et al., "Suppression of Experimental Allergic Encephalomyelitis in Rhesus Monkeys by a Synthetic Basic Copolymer", *Clin. Immunol. Immunopath.*, 1974, 3, 256-262.

Webb, et al., "Suppression of Experimental Allergic Encephalomyelitis in Rhesus Monkeys by a Synthetic Basic Copolymer", *Isr. J. Med. Sci.*, 1975, 11, 1388 (Abstract).

Webb, et al., "Molecular Requirements Involved in Suppression of EAE by Synthetic Basic Copolymers of Amino Acids", *Immunochem.*, 1976, 13, 333-337.

Abramsky, et al., "Effect of a Synthetic Polypeptide (COP-1) on Patients with Multiple Sclerosis and with Acute Disseminated Encephalomyelitis", *J. Neurol. Sci.*, 1977, 31, 433-438.

Teitelbaum, et al., "Suppression of Experimental Allergic Encephalomyelitis in Baboons by Cop 1", *Israel J. Med. Sci.*, 1977, 13, 1038 (Abstract).

Arnon, et al., "Suppression of EAE in Baboons by a Synthetic Polymer of Amino Acids", *Neurol.*, 1978, 28, 336 (Abstract).

Sela, et al., "Experimental Allergic Encephalomyelitis" in *Menarini Series on Immunopathology, vol. 1, First Symposium of Organ Specific Autoimmunity*, Cremona, Italy, Jun., 1977, (Miescher P.A. ed., Schwabe Co., Basel, 1978), 9-21.

Alvord, et al., "Myelin Basic Protein Treatment of Experimental Allergic Encephalomyelitis in Monkeys", *Ann. Neurol.*, 1979, 6, 469-473.

Keith, et al., "The Effect of COP 1, a Synthetic Polypeptide, on Chronic Relapsing Experimental Allergic Encephalomyelitis in Guinea Pigs"*J. Neurol. Sci.*, 1979, 42, 267-274.

Lando, et al., "Effect of Cyclophosphamide on Suppressor Cell Activity in Mice Unresponsive to EAE", *J. Immunol.*, 1979, 123, 2156-2160 (Abstract).

Lando, et al., "Experimental Allergic Encephalomyelitis in Mice—Suppression and Prevention with COP-1", *Israel J. Med. Sci.*, 1979, 15, 868-869 (Abstract).

Teitelbaum, et al., "Blocking of Sensitization to Encephalitogenic Basic Protein in Vitro by Synthetic Basic Copolymer (COP 1)" in *Cell Biology and Immunology of Leukocyte Function* (Academic Press, New York, 1979) 681-685.

Teitelbaum, "Suppression of Experimental Allergic Encephalomyelitis with a Synthetic Copolymer—Relevance to Multiple Sclerosis", in *Humoral Immunity in Neurological Diseases* (Karcher D., Lowenthal A. & Strosberg A.D., eds., Plenum Publishing Corp., 1979) 609-613.

Arnon, et al., "Desensitization of Experimental Allergic Encephalomyelitis with Synthetic Peptide Analogues" in *The Suppression of Experimental Allergic Encephalomyelitis and Multiple Sclerosis* (Academic Press, New York, 1980) 105-107.

Arnon, "A Synthetic Copolymer of Amino Acids in a Clinical Trial for MS Therapy" in *Progress in Multiple Sclerosis Research*(Bauer, Ritter, eds., Springer Verlag New York, 1980) 416-418.

Bornstein, et al., "Treatment of Multiple Sclerosis with a Synthetic Polypeptide: Preliminary Results", *Ann. Neurol.*, 1980, 8, 117 (Abstract).

Bornstein, et al., "Treatment of Multiple Sclerosis with a Synthetic Polypeptide: Preliminary Results", *Trans. Am. Neurol. Assoc.*, 1980, 105, 348-350.

McDermott, et al., "Antigen-induced Suppression of Experimental Allergic Neuritis in the Guinea Pig", *J. Neurol. Sci.*, 1980, 46, 137-143.

Arnon, "Experimental Allergic Encephalomyelitis—Susceptibility and Suppression", *Immunological Rev.*, 1981, 55, 5-30.

Bornstein, et al., "Multiple Sclerosis: Trial of a Synthetic Polypeptide", *Ann. Neurol.*, 1982, 11, 317-319.

Brosnan, et al., "The Response of Normal Human Lymphocytes to Copolymer 1", *J. Neuropath. Exp. Neurol.*, 1983, 42, 356 (Abstract).

Lisak, et al., "Effect of Treatment with Copolymer 1 (Cop-1) on the in Vivo and in Vitro Manifestations of Experimental Allergic Encephalomyelitis (EAE)", *J. Neurol. Sci.*, 1983, 62, 281-293.

Bornstein, et al., "Clinical Trials of Copolymer 1 in Multiple Sclerosis", *Ann, N.Y. Acad. Sci.* (*USA*), 1984, 366-372.

Bornstein, et al., "Clinical Trials of a Synthetic Polypeptide (Copolymer 1) for the Treatment of Multiple Sclerosis" in Gonsett et al., *Immunological and Clinical Aspects of Multiple Sclerosis* (MTP Press, The Hague, 1984) 144-150.

Brosnan, et al., "Copolymer 1: Effect on Normal Human Lymphocytes", *Ann. N.Y. Acad. Sci.* (*USA*), 1984, 436, 498-499.

Bornstein, et al., "Multiple Sclerosis: Clinical Trials of a Synthetic Polypeptide, Copolymer 1", *Neurol.*, 1985, 35 (Suppl. 1), 103 (Abstract).

Brosnan, et al., "Immunogenic Potentials of Copolymer 1 in Normal Human Lymphocytes", *Neurol.*, 1985, 35, 1754-1759.

Burns, et al., "Human Cellular Immune Response in Vitro to Copolymer 1 and Myelin Basic Protein (MBP)", *Neurol.*, 1985, 35 (Suppl. 1), 170 (Abstract).

Teitelbaum, et al., "Monoclonal Antibodies to Myelin Basic Protein Cross React with Synthetic EAE-suppressive Copolymer, COP 1" in *Proc. 7th Eur. Immunol. Mtg.*, Jerusalem, Sep. 8-13, 1985 (Abstract).

Thompson, "MCQ Tutor: Medical Immunology Multiple Choice Questions", *Immunol. Today*, 1985, 6(4), 141.

Burns, et al., "Human Cellular Immune Response to Copolymer 1 and Myelin Basic Protein", *Neurol.*, 1986, 36, 92-94.

Bornstein, "Cop 1 May be Beneficial for Patients with Exacerbating-remitting Form of Multiple Sclerosis", *Adv. Ther. (USA)*, 1987, 4, 206 (Abstract).

Bornstein, et al., "A Pilot Trial of Cop 1 in Exacerbating-remitting Multiple Sclerosis", *New Eng. J. Med.*, 1987, 317(7), 408-414.

Rolak, "Copolymer-I Therapy for Multiple Sclerosis", *Clin. Neuropharmacology*, 1987, 10(5), 389-396.

Winer, "COP 1 Therapy for Multiple Sclerosis", *New Eng. J. Med.*, 1987, 317(7), 442-444.

Arnon, et al., "Suppression of Demyelinating Diseases by Synthetic Copolymers", in *A Multidisciplinary Approach to Myelin Disease* (G. Serlupi Crescenzi, ed., Plenum Publishing Corp., 1988) 243-250.

Baumhefner, et al., "Copolymer 1 as Therapy for Multiple Sclerosis: The Cons", *Neurol.*, 1988, 38(Suppl. 2), 69-71.

Bornstein, et al., "Clinical Experience with COP-1 in Multiple Sclerosis", *Neurol.*, 1988, 38(Suppl. 2), 66-69.

Teitelbaum, et al., "Specific Inhibition of the T-cell Response to Myelin Basic Protein by the Synthetic Copolymer Cop 1", *Proc. Natl. Acad. Sci. USA*, 1988, 85, 9724-9728.

Arnon, et al., "Suppression of Experimental Allergic Encephalomyelitis by Cop-1—Relevance to Multiple Sclerosis", *Israel J. Med. Sci.*, 1989, 25, 686-689.

Bornstein, et al., "Pilot Trial of COP-1 in Chronic Progressive Multiple Sclerosis: Preliminary Report", from *The International Multiple Sclerosis Conference: An Update on Multiple Sclerosis*, Roma (Italy), Sep. 15-17, 1988, in *Elsevier Science Publisher*, 1989, 225-232.

Teitelbaum, et al., "Clinical Trial of Copolymer 1 in Multiple Sclerosis"*J. Israel Med. Assoc.*, 1989, CXVI(9), 453-456.

Bornstein, et al., "Clinical Trials of Cop 1 in Multiple Sclerosis" in *Handbook of Multiple Sclerosis* (S.D. Cook Marcel Rekker, ed., 1990) 469-480.

Carter, et al., "Newer Drug Therapies for Multiple Sclerosis", *Drug Therapy*, 1990, 31-32, 37-39, 42-43.

Grgacic, et al., "Cell-mediated Immune Response to Copolymer 1 in Multiple Sclerosis Measured by the Macrophage Procoagulant Activity Assay", *Int. Immunol.*, 1990, 2(8), 713-718.

Kay, et al., "The Mechanism of Action of FK 506", *Transplantation Proceedings*, 1990, 22(1, Suppl. 1), 96-99.

Lee, et al., "Peptide and Protein Drug Delivery" in *Advances in Parenteral Sciences* (Vincent H.L. Lee, ed., Marcel Dekker, Inc., 1990) 691-695.

Myers, et al., "The Peculiar Difficulties of Therapeutic Trials for Multiple Sclerosis", *Neurologic Clinics*, 1990, 8(1), 119-141.

Sela, et al., "Suppressive Activity of COP-1 in EAE and its Relevance to Multiple Sclerosis", *Bull. Inst. Pasteur*, 1990, 88, 303-314.

Starzl, *Transplantation Proceedings*, 1990, 22 (1, Suppl. 1), 5.

Wender, "Copolymer 1 (COP-1) in the Treatment of Multiple Sclerosis (letter)" *Neur. Neurochir. Pol.*, 1990, 24, 113.

Bornstein, et al., "A Placebo-controlled, Double-blind, Randomized Two-center, Pilot Trial of Cop 1 in Chronic Progressive Multiple Sclerosis", *Neurol.*, 1991, 41, 533-539.

Burns, et al., "Failure to Copolymer 1 to Inhibit the Human T-cell Response to Myelin Basic Protein", *Neurol.*, 1991, 41, 1317-1319.

Clinical Trial Protocol No. 9001, Teva Pharmaceutical Industries, Ltd., first patient enrolled Oct. 23, 1991.

Ferrara, et al., "Graft-Versus-Host Disease", *New Eng. J. Med.*, 1991, 324, 667-674.

Meiner, "COP-1 Multicenter Clinical Trial in Exacerbating-remittin Multiple-Sclerosis: One Year Follow-up", *J. Neurol.*, 1991(Suppl. 1) (Abstract).

Rothbard, et al., "Interactions Between Immunogenic Peptides and MHC Proteins", *Ann. Rev. Immunol.*, 1991, 9, 527-565.

Salvetti, et al., "Myelin Basic Protein T Cell Epitopes in Patients with Multiple Sclerosis", *Department of Neurological Sciences, University of Rome, La Sapienza* 1991, 72 (Abstract).

Teitelbaum, et al., "Cross-reactions and Specificities of Monoclonal Antibodies Against Myelin Basic Protein and Against the Synthetic Copolymer 1", *Proc. Natl. Acad. Sci. (USA)*, 1991, 88, 9528-9532.

Van den Bogaerde, et al., "Induction of Long-Term Survival of Hamster Heart Xenografts in Rats", *Transplantation*, 1991, 52, 15-20.

Bornstein, et al., "Treatment of Multiple Sclerosis with Copolymer 1" in *Treatment of Multiple Scleorsis: Trial Design, Results and Future Perspectives* (Rudick R.A. & Goodkin D.E., eds., Springer Verlag, London, 1992) 173-198.

Johnson, "Clinical Studies in Copolymer 1 Therapy for Exacerbating-remitting Multiple Sclerosis", in *Congress for Advances in the Understanding and Treatment of Multiple Sclerosis*, Boston (USA), Oct. 28-29,1992.

Milo, et al., "Inhibition of Myelin Basic Protein-specific Human T-cell Lines by COP-1", *Israel J. Med. Sci.*, 1992, 28, 486 (Abstract).

Racke, et al., "Copolymer-1-induced Inhibition of Antigen-specific T Cell Activation: Interference with Antigen Presentation", *J. Neuroimmunol.*, 1992, 37, 75-84.

Teitelbaum, et al., "Synthetic Copolymer 1 Inhibits Human T-cell Lines Specific for Myelin Basic Protein", *Proc. Natl. Acad. Sci. (USA)*, 1992, 89, 137-141.

Weinshenker et al., "Natural History and Treatment of Multiple Sclerosis", *Current Opinion in Neurol. and Neurosurgery*, 1992, 5, 203-211.

Aharoni, et al., "T Suppressor Hybridomas and Interleukin-2-Dependent Lines Induced by Copolymer 1 or by Spinal Cord Homogenate Down-Regulate Experimental Allergic Encephalomyelitis", *Eur. J. Immunol.*, 1993, 23, 17-25.

Arnon, et al., "Immunomodulation of Experimental Allergic Encephalomyelitis", *Israel J. Med. Sci.*, 1993, 29, 175-181.

Arnon, et al., "On the Existence of Suppressor Cells", *Int. Arch. Allergy Immunol.*, 1993, 100, 2-7.

Clinical Trial Protocol No. 9002, Lemmon Co. and Teva Pharmaceutical Industries, Ltd., first patient enrolled Jun. 17, 1993.

Francis, "The Current Therapy of Multiple Sclerosis", *J. Clin. Pharmacy and Therapeutics*, 1993, 18, 77-84.

Keleman, et al., "Graft-versus-Host Disease in Bone Marrow Transplantation: Experimental, Laboratory, and Clinical Contributions of the Last Few Years", *Int. Arch. Allergy Immunol.*, 1993, 102, 309-320.

Gurevich, "Study of the MHC-competition Between BP and Cop 1 Using Human Cytotoxic T-cell Clones", *Israel J. Med. Sci.*, 1993 (Abstract).

Meiner, et al., "The Israeli COP-1 Multicenter Clinical Trial in Exacerbating-remitting Multiple Sclerosis—Two-year Follow-up", in 9th *Congress of the European Committee for Treatment and Research in Multiple Sclerosis*, Florence (Italy), Oct.-Nov., 1993, 48 (Abstract).

Milo, et al., "Copolymer-1 (COP-1) Regulates Class II MHC Expression and Cytokine Synthesis in the THP-1 Monocyte-Macrophage Cell Line" in *The IBC Conference on Multiple Sclerosis*, San Diego (USA), Dec. 10, 1993 (Abstract).

Sela, "Polymeric Drugs as Immunomodulatory Vaccines Against Multiple Sclerosis", *Makromol. Chem. Macromol. Symp.*, 1993, 70/71, 147-155.

Arnon, et al., "Immunospecific Drug Design—Prospects for Treatment of Autoimmune Disease", *Therapeutic Immunol.*, 1994, 1, 65-70.

Bansil, et al., "Multiple Sclerosis: Pathogenesis and Treatment", *Seminars in Neurol.*, Jun. 1994, 14(2), 146-153.

The COP-1 Multicenter Clinical and Research Group Study, "COP-1 Multicenter Trial in Relapsing Remitting Multiple Sclerosis: 3 Year Follow Up", *Abstracts of Symposia and Free Communication*, Barcelona (Spain), Jun. 25-29, 1994, 241 (Suppl. 1), 6.

Cotton, "Options for Multiple Sclerosis Therapy", *J.A.M.A. Medical News & Perspectives*, 1994, 272(18), 1393.

Dorling, et al., "Prospects for Xenografting", *Curr. Opinions Immunol.*, 1994, 6, 765-769.

Fridkis-Hareli, et al., "Copolymer 1 Displaces MBP, PLP and MOG, but Can Not be Displaced by these Antigens from the MHC Class II Binding Site", *Department of Chemical Immunology, The Weizmann Institute of Science*, 1994.

Fridkis-Hareli, et al., "Direct Binding of Myelin Basic Protein and Synthetic Copolymer 1 to Class II Major Histocompatibility Complex Molecules on Living Antigen-Presenting Cells—Specificity and Promiscuity", *Proc. Natl. Acad. Sci. USA*, 1994, 91, 4872-4876.

Fridkis-Hareli, et al., "Specific and Promiscuous Binding of Synthetic Copolymer 1 to Class II Major Histocompatibility Complex Molecules on Living Antigen Presenting Cells", *Israeli Biochem. Soc.*, 1994, 21-22 (Abstract).

Fridkis-Hareli, et al., "Synthetic Copolymer 1 Inhibits the Binding of MBP, PLP and MOG Peptides to Class II Major Histocompatibility Complex Molecules on Antigen Presenting Cells" In *Neurochem Mtg.*, Aug. 14-19, 1994.

Fridkis-Hareli, et al., "Synthetic Copolymer 1 Inhibits the Binding of MBP, PLP and MOG Peptides to Class II Major Histocompatibility Complex Molecules on Antigen-Presenting Cells", *J. Neurochem.*, 1994, 63 (Supp. I), 561.

Fridkis-Hareli, et al., "Synthetic Copolymer 1 and Myelin Basic Protein Do Not Undergo Processing Prior to the Binding to Class II Major Histocompatibility Complex Molecules on Antigen Presenting Cells", *Israeli Immunol. Soc.*, May 3-4, 1994 (Abstract).

Fridkis-Hareli, et al., "Synthetic Copolymer 1 and Myelin Basic Protein do not Require Processing Prior to Binding to Class II Major Histocompatibility Complex Molecules on Living Antigen Presenting Cells", *Department of Chemical Immunology, The Weizmann Institute of Science*, Rehovot, Israel, 1994.

Fridkis-Hareli, et al., "Synthetic Copolymer 1 and Myelin Basic Protein Do Not Require Processing Prior to Binding to Class II Major Histocompatibility Complex Molecules on Living Antigen-Presenting Cells", *Cell. Immunol.*, 1995, 163, 229-236.

Jacobs et al., "Advances in Specific Therapy for Multiple Sclerosis", *Neurol.*, 1994, 7, 250-254.

Johnson, "Experimental Therapy of Relapsing-Remitting Multiple Sclerosis with Copolymer-1", *Ann. Neurol.*, 1994, 36(Suppl.), 115-117.

Kott, et al., "COP-1 Increases Suppressor Cells Number in Multiple Sclerosis", *Israel Neurological Assoc.*, Dec. 19-20, 1994, Herzliya (Israel), 17.

Mengle-Gaw, "The Major Histocompatibility Complex (MHC)", in *Encycl. Molecular Bio.* (Oxford Blackwell Science Ltd, 1994) 602-606.

Milo, et al., "Additive Effects of COP-1 and IFN-Beta on Immune Responses to Myelin Basic Protein", *Neurol.*, 1994, 44(Suppl. 2), A212.

Milo, et al., "Additive Effect of Copolymer-1 and Interferon-β on the Immune Response to Myelin Basic Protein", *Assaf Harofeh Medical Center, Sackler School of Medicine, Tel-Aviv University of Maryland School of Medicine*, 1994, 22.

Milo, et al., "Copolymer-1 and Interferon-β Additively Suppress the Immune Response to Myelin Basic Protein by Inhibiting Antigen Presentation", *J. Neuroimmunol.*, 1994, 54, 183 (Abstract).

Nightingale, et al., "Access to Investigational Drugs for Treatment Purposes", *Am. Family Physician*, 1994, 50(4), 845-847.

Schlegel, et al., "Prevention of Graft-Versus-Host Disease by Peptides Binding to Class II Major Histocompatibility Complex Molecules", *Blood*, 1994, 84(8), 2802-2810.

Stark, "Expanded Clinical Trials of Treatments for Multiple Sclerosis (MS) : Copolymer 1 (COP-1) Treatment Investigational New Drug (IND) Program", *Ann. Neurol.*, 1994, 36, 114-115.

Teitelbaum, et al., "Immunological Parameters in a Multicenter Clinical Trial of COP1 in Multiple Sclerosis (MS) : A 2-year Follow-up", *Neurol.*, 1994, 44(Suppl. 2) , A358.

Tisch et al., "Antigen-specific immunotherapy: Is it a Real Possibility to Combat T-Cell-Mediated autoimmunity?" *Proc. Natl. Acad. Sci. U.S.A.*, 1994, 91, 437-438.

Milo, et al., "Additive Effects of Copolymer-1 and Interferon β -1b on the Immune Response to Myelin Basic Protein", *J. Neuroimmunol.*, 1995, 61, 185-193.

O'Connor, et al., "Powders" in *The Science and Practice of Pharmacy*, Remington, 1995, 2, 1598-1614.

Porter, "Coating of Pharmaceutical Dosage Forms," in *The Science and Practice of Pharmacy*, Remington, 1995, 2, 1650-1659.

Reilly, Jr., W.J., "Pharmaceutical Necessities" in *The Science and Practice of Pharmacy*, Remington, 1995, 2, 1380-1416.

Schlegel, et al., "Inhibition of Allorecognition and Prevention of Graft-vs-host Disease (GVHD) by GLAT, a Synthetic Polymer with Promiscuous Binding to Murine and Human MHC Class II Molecules", in *Am. Soc. Hematology, 37th Annual Meeting*, Seattle, WA (USA) , Dec. 1-5, 1995, 224a (Abstract).

Ben-Nun, et al., "The Autoimmune Reactivity to Myelin Oligodendrocyte Glycoprotein (MOG) in Multiple Sclerosis is Potentially Pathogenic: Effect of Copolymer 1 on MOG-induced Disease", *J. Neurol.*, 1996, 243 (Suppl. 1), S14-S22.

Johnson, Management of Relapsing/Remitting Multiple Sclerosis with Copolymer 1 (Copaxone) , *Chemical Abstracts*, 1996, 125, 291993b.

Sykes, "Immunobiology of Transplantation", *Faseb J.*, 1996, 10, 721-730.

Teitelbaum, et al., "Copolymer 1 Inhibits Chronic Relapsing Experimental Allergic Encephalomyelitis Induced by Proteolipid Protein (PLP) Peptides in Mice and Interferes with PLP-specific T Cell Responses", *J. Neuroimmunol.*, 1996, 64, 209-217.

Aharoni, et al., "Studies on the Mechanism and Specificity of the Effect of the Synthetic Random Copolymer GLAT on Graft-versus-Host Disease", *Immunol. Letters*, 1997, 58, 79-87.

Puri et al., "Modulation of the Immune Response in Multiple Sclerosis", *J. Immunol*, 1997, 158, 2471-2476.

Tarcic et al., "Copolymer 1 (Copaxone) from an Idea to a Drug for Treatment of Multiple Sclerosis" Database HCAPLUS on STN, Israel: AN 1997:333270. Kim, Handasa Kim, 1997, 281(14), 16-18 (Abstract)

Teitelbaum, et al., "Copolymer 1 from the Laboratory to FDA", *Israel J. Med. Sci.*, 1997, 33, 280-284.

Fridkis-Hareli, et al., "Promiscuous Binding of Synthetic Copolymer 1 to Purified HLA-DR Molecules", *J. Immuno.*, 1998, 160, 4386-4397.

Fridkis-Hareli, et al., "Synthetic Amino Acid Copolymers that Bind to HLA-DR Proteins and Inhibit Type II Collagen-reactive T Cell Clones", *Proc. Natl. Acad. Sci.*, Oct. 1998, 95, 12528-12531.

Cazzato, et al., "Treatment of Multiple Sclerosis. The Present and the Future. Study Group on Diagnosis and Therapy of Multiple Sclerosis", Database Medline on STN, Instituto do Clinica Neurologica, Universitá, Trieste, Italy: Medline AN: 2000060325, Recent Progressi in Medicina. Oct. 1999, 90 (10), 538-544 (Abstract).

Kepsutlu et al., "Evaluation of Chitosan Used as an Excipient in Tablet Formulations", Database HCAPLUS on STN, Department of Pharmaceutical Technology, Gulhane Military Medical Academy, Ankara, 06018, Turkey, HCAPLUS AN: 1999: 590411, Acta. Pol. Pharm. 1999, 56(3), 227-235 (Abstract).

Prat, et al., "Lymphocyte Migration and Multiple Sclerosis: Relation with Disease Course and Therapy," *Ann. Neurol.*, 46, 253-256 (1999).

Fridkis-Hareli et al., "Synthetic Peptides that Inhibit Binding of the Collagen Type II 261-273 Epitope to Rheumatoid Arthritis-Associated HLA-DR1 and DR4 Molecules and Collagen-Specific T-cell Responses", Database HCAPLUS on STN, Department of Clinical Immunology, Aarhus University Hospital, Aarhus, Denmark, HCAPLUS AN: 2000:455053, Human Immunology, 2000, 61(7), 640-650 (Abstract).

Durelli, "Immunotherapeutics of Multiple Sclerosis", "Instituto di Clinica delle Malattie del Sistema Nervoso Universita di Torino", 467-475.

Harrison and Hafler, "Antigen-Specific Therapy for Autoimmune Disease", *Current Opin. Immunol.*, 2000, 12(6): 704-711.

Pender at al., *Int. Med. Journal*, 2002, 32: 554-563.

Van Noort at al., *International Review of Cytology*, 1995, 178: 127-205.

Webster's II New Riverside University Dictionary, The Riverside Publishing Company, 1984, 933.

U.S. Appl. No. 09/359,099, filed Jul. 22, 1999, Strominger et al.

U.S. Appl. No. 09/487,793, filed Jan. 20, 2000, Eisenbach-Schwartz et al.

U.S. Appl. No. 09/620,216, filed Jul. 20, 2000, Eisenbach-Schwartz et al.

Aharoni, et al., "Copolymer 1 induces T cells of the T helper type 2 that crossreact with myelin basic protein and suppress experimental autoimmune encephalomyelitis", *Proc. Natl. Acad. Sci. USA*, 1997, 94, 10821-10826.

Aharoni, et al., "COP 1 Specific Supporessor Cells Inhibit Experimental Allergic Encephalomyelitis Induced by Either Mouse Spinal Cord Homogenate or Proteolipid Protein Peptide 139-151", Neurology, 1997, vol. 48, No. 3, A422.

Aharoni et al., "Bystander Suppression of Experimental Autoimmune Encephalomyelitis by T Cell Lines and Clones of the Th2 Type Induced by Copolymer 1", *J. Neuroimmunol.* 1998, 91(1-2), 135-146.

Asakura et al., "A unique population of circulating autoantibodies promotes central nervous system remyelination", *Multiple Sclerosis*, 1998, 4, 217-221.

Asakura et al., "Targeting of IgMk Antibodies to Oligodendrocytes Promotes CNS Remyelination", The *Journal of Neuroscience*, 1998, 18(19), 1700-1108.

Bieber, et al., "Antibody-mediated remyelination: relevance to multiple sclerosis", *Multiple Sclerosis*, 2000, 6(2), S1-S5.

Bieber, et al., "Humoral autoimmunity as a mediator of CNS repair", *A Trends Guide to Neurodegenerative Disease and Repair/Review*, 2001, 24(11), S39-S44.

Duda, et al., "Human and Murine CD4 T Cell Reactivity to a Complex Antigen: Recognition of the Synthetic Random Polypeptide Glatiramer Acetate", The Journal of Immunology, 2000, 165, 7300-7307.

Johnson, et al. "Copolymer 1 reduces relapse rate and improves disability in relapsing-remitting multiple sclerosis: results of a phase III multicenter, double-blind placebo-controlled trial. The Copolymer 1 Multiple Sclerosis Study Group", Neurology, 45(7), 1268 (abstract).

Lovell, K. and Jones, M., "CNS Infections, Spongiform Encephalopathy and Demyelinating Diseases," Karol Marcinkowski U. Med. Sci., Dept. Pathol., Poland [online] [retreived on Apr. 19, 2003]. Retrieved from internet: <URL: http://ampat.amu.edu.pl/guzyuno/CNS_INFE.HTM>.

McGavern, et al. "Do Antibodies Stimulate Myelin Repair in Multiple Sclerosis?", The Neuroscientist, 1999, 5(1), 19-28.

*Merck Manual of Diagnosis and Therapy*, Merck Research laboratories, Whitehouse Station, N.J., 17th Ed., 1999, 1300-1303, 1312-1317.

Pavelko, et al., "Acceleration in the Rate of CNS Remyelination in Lysolecithin-Induced Demyelination", *The Journal of Neuroscience*, 1998 18(7), 2498-2505.

Pharmacia Biotech Directory, 1996, pp. 340-341.

Physician's Desk Reference, 2000, Medical Economics Co. Inc., Montvale, NJ, 3115.

Rodriguez, et al., *Neurological Therapeutics*, 1998, 15(3): 245-250.

Sela, M., et al., "Sythetic Approaches to Vaccines for Infectious and Autoimmune Diseases" Vaccine, 1992, vol. 10, Issue 14, 991-999.

Teva, et al., "Copolymer-1 Glatiramer Acetate Copaxone Agent for Multiple Sclerosis", Drugs of the Future, 1998, vol. 23, No. 2, 213-214.

Warrington, et al., "Human monoclonal antibodies reactive to oligodenrocytes promote remyelination in a model of multiple sclerosis", PNAS, 2000, 97(12), 6820-6825.

Warrington, et al., "Immunoglobulin-mediated CNS repair", J. Allergy Clin. Immunol., 2001, S121-S125.

Wiesemann, et al., "Glatiramer Acetate (GA) induces IL-13/IL-5 secretion in naive T cells", Journal of Neuroimmunology, 2001, 119, 137-144.

Lampert, et al., "Expression of Matrix Matalloproteinases and Their Inhibitors in Human Brain Tumors", American Journal of Pathology, vol. 153, No. 2, 1998, 429-437.

Pereira, et al., "The Blood-Brain Barrier in HIV-associated Dementia", NeuroAids, vol. 3, No. 2, 2000.

Kieseier, et al., "Differential Expression of Matrix Matalloproteinases in Bacterial Menigitis", Brain, 1999, 122: 1579-1587.

* cited by examiner

ORAL, NASAL AND PULMONARY DOSAGE FORMULATIONS OF COPOLYMER 1

This application is a continuation-in-part of and claims the benefit of U.S. Provisional Application No. 60/183,666, filed Feb. 18, 2000, the contents of which are hereby incorporated by reference.

Throughout this application, various references are cited. These publications, in their entireties, are hereby incorporated by reference to more fully describe the state of the art to which the invention pertains.

INTRODUCTION

The present invention provides oral, nasal and pulmonary dosage formulations of Copolymer 1. COPAXONE® is the brand name for glatiramer acetate (also known as Copolymer 1). Glatiramer acetate (GA), the active ingredient of COPAXONE®, consists of the acetate salts of synthetic polypeptides, containing four naturally occurring amino acids: L-glutamic acid, L-alanine, L-tyrosine, and L-lysine with average molar fractions of [L-Glu: 0.129–0.153; L-Ala: 0.392–0.462; L-Tyr: 0.086–0.100; L-Lys: 0.300–0.374] respectively. The average molecular weight of glatiramer acetate is 4,700–11,000 daltons. Chemically, glatiramer acetate is designated L-glutamic acid polymer with L-alanine, L-lysine and L-tyrosine, acetate (salt). Its structural formula is:

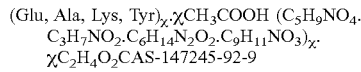

("Copaxone", *Physician's Desk Reference*, (2000), Medical Economics Co., Inc., (Montvale, N.J.), 3115.) Glatiramer acetate is also written as: poly [L-Glu$^{13-15}$, L-Ala$^{39-46}$, L-Tyr$^{8.6-10}$, L-Lys$^{30-37}$].n CH$_3$COOH. Copolymer 1 is widely believed to be effective in treating a variety of immune system conditions. A common method of administering the drug is subcutaneous injection. However, such administration often results in injection site reactions such as irritation, hypersensitivity, inflammation and pain. In addition, it tends to be difficult to persuade patients to adhere to the prescribed dosing regimes. To overcome these difficulties, oral, nasal and pulmonary dosage formulations are desirable. This invention provides compositions of and processes for creating solid, semisolid and aqueous dosage forms intended for oral, nasal and pulmonary administration.

BACKGROUND OF THE INVENTION

Autoimmune diseases occur when a mammal's immune system fails to recognize some of the mammal's own tissues as "self" and attacks them as "foreign". Normally, self-tolerance is developed early by developmental events within the immune system that prevent the mammal's T cell and B cells from reacting with the mammal's own tissues. Major Histocompatibility Complex (Major Histocompatibility Complex) cell surface proteins help regulate these early immune responses by binding to and presenting processed peptides to T cells.

When this self-tolerance breaks down, autoimmune diseases develop. Now, the mammal's own tissues and proteins are recognized as "antigens" and are attacked by the mammal's immune system. For example, multiple sclerosis is believed to be an autoimmune disease that occurs when the immune system attacks the myelin sheath. This sheath is thought to insulate and protect the nerves. The disease is a progressive one, characterized by demyelination, followed by neuronal loss and motor function loss. An additional example is rheumatoid arthritis ("RA"). RA is believed to be an autoimmune disease arthritis ("RA"). RA is believed to be an autoimmune disease which involves chronic inflammation of the synovial joints and infiltration by activated T cells, macrophages and plasma cells. This inflamation is thought to lead to a progressive destruction of the articular cartilage. It is the most severe form of joint disease. The nature of the autoantigen(s) attacked in rheumatoid arthritis is poorly understood, but collagen type II is a candidate.

Like autoimmune diseases, rejection of transplanted tissue also involves a hyper-response by the immune system to an antigen. This is manifested as graft rejection in the case of organ transplantation (host-versus-graft disease, or HVGD). Another manifestation of pathological immune reactivity is graft-versus-host disease (GVHD) that occurs in approximately 30% of bone marrow recipients. Up to half of those patients who develop GVHD may succumb to this process. This high morbidity and mortality has led to continuous interest in the possibility of controlling or preventing GVHD.

There are two forms of GVHD, acute and chronic. Acute GVHD develops within the first 3 months after bone marrow transplantation and features disorders of skin, liver and gastrointestinal tract. Chronic GVHD is a multiorgan autoimmune-like disease, emerging from 3 months up to 3 years post-transplantation and shares features common to naturally occurring autoimmune disorders, like systemic lupus erythematosus (SLE) and scleroderma.

Studies on the effect of Copolymer 1 on various processes involved in the pathological course of immune rejection showed that Copolymer 1 inhibited T cell proliferation in response to host cell (Aharoni et al., Immunology Letters 58(2):79–87, 1997). Copolymer 1 treatment completely abolished cytotoxic activity toward grafts, prevented the pro-GVHD IL-2 and IFN-γ cytokine secretion, and induced beneficial Th2 anti-inflammatory response. In view of these cumulative data, Copolymer 1 is a candidate drug for the prevention of HVGD and GVHD in humans. See WO 96/32119 and U.S. Pat. No. 5,858,964. Copolymer 1 has been suggested as a potential therapeutic agent for multiple sclerosis (*Eur. J. Immunol.* [1971] 1:242; and *J. Neurol. Sci.* [1977] 31:433; K. P. Johnson, 1 *Neurology* 65–70 (1995); *N. Engl. J. Med.* [1987] 317:408) and other immune system conditions, such as immune diseases and delayed-type hyper-sensitivity conditions (WO 00/05250). This drug is a synthetic polypeptide functionally crossreactive with myelin basic protein (MBP). MBP is a natural component of the myelin sheath.

Copolymer 1 has been shown to suppress experimental allergic encephalomyelitis (EAE) induced by various encephalitogens, including mouse spinal cord homogenate (MSCH). MSCH encompasses all myelin antigens, such as MBP (Sela M. et aL., 88 *Bull. Inst. Pasteur* 303–314 (1990), proteolipid protein (PLP) (Teitelbaum, D. et al., *J. Neuroimmunol.* (1996) 64:209–217) and myelin oligodendrocyte glycoprotein (MOG) (Ben-Nun A et al., 243 J. Neurol. (Suppl 1) S14–S22 (1996)) in a variety of species. EAE is an accepted model for multiple sclerosis.

It has also been demonstrated that Copolymer 1 is active when injected subcutaneously, intra-peritoneally, intravenously or intramuscularly (D. Teitelbaum et al., *Eur. J. Immunol.* (1971) 1:242–248; D. Teitelbaum et al., *Eur. J. Immunol.* (1973) 3:273–279). For instance, in phase III clinical trials, daily subcutaneous injections of Copolymer 1 were found to slow progression of disability and reduce the relapse rate in exacerbating-remitting multiple sclerosis (K. P. Johnson, 1 Neurology 65–70 (1995); N. Engl. J. Med. [1987] 317:408).

Currently, all approved treatments of multiple sclerosis involve subcutaneous injection of the active substance. Frequently observed injection-site reactions include irritation, hypersensitivity, inflammation and pain and even necrosis (in the case of at least one interferon β 1-b treatment) and a low level of patient compliance. Therefore, an alternative method of administration is desirable. Thus, in order to effectively treat chronic diseases such as autoimmune diseases, oral, nasal or pulmonary formulations and methods for producing such formulations are necessary.

One way to overcome the difficulties in subcutaneous injection of drugs is to create a form that can be taken orally. EP Patent 359,783 discloses the treatment of autoimmune disease by oral administration of autoantigens. In addition, it describes the oral administration of MBP for the treatment of multiple sclerosis. Oral administration of an autoantigen has been termed "oral tolerance".

PCT International Application Nos. WO 91/12816, WO 91/08760, and WO 92/06704 all depict the treatment of autoimmune diseases other than multiple sclerosis using the "oral tolerance" method with a variety of autoantigens. However, none of these references disclose the treatment of multiple sclerosis or other autoimmune diseases by the oral administration of a non-autoantigen such as Copolymer 1.

The invention also encompasses another avenue of administration that avoids the problems inherent in subcutaneous injection. This avenue is to produce a form of the drug that can be administered nasally.

SUMMARY OF THE INVENTION

The disclosed invention provides pharmaceutical compositions useful for treating autoimmune diseases in a mammal comprising as an active ingredient a therapeutically effective amount of Copolymer 1, and microcrystalline cellulose. Processes for the manufacture of such compositions are also disclosed.

DETAILED DESCRIPTION OF THE INVENTION

Figure 1:
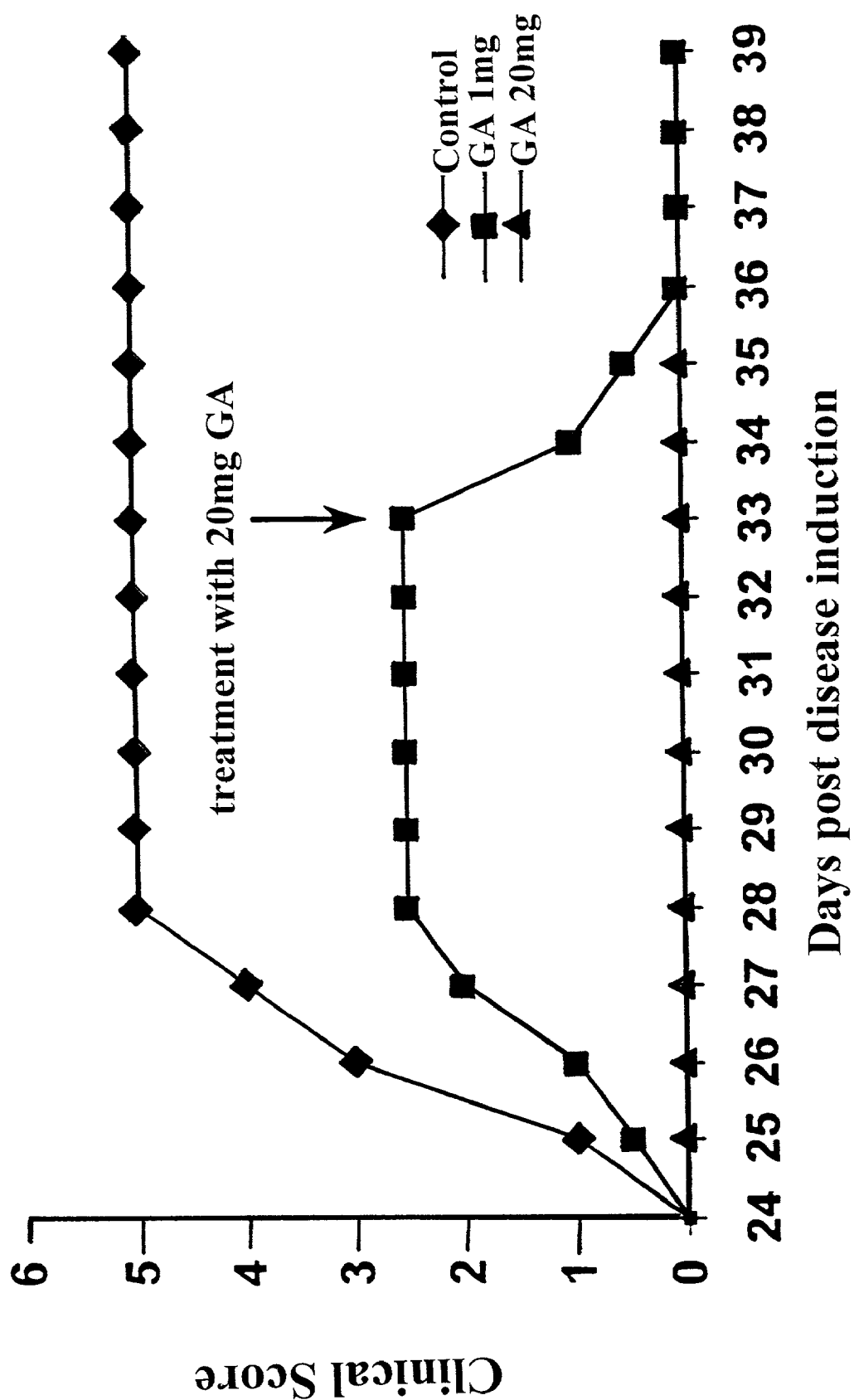
FIG. 1 shows the results of trials ascertaining prevention and treatment of EAE in Rhesus monkeys fed with Copolymer 1 (glatiramer acetate—"GA") enteric coated capsules.

This invention provides a pharmaceutical composition comprising as an active ingredient a therapeutically effective amount of Copolymer 1, and microcrystalline cellulose.

The amount of microcrystalline cellulose is at least 50% by weight, preferably from about 60% to about 90% by weight, more preferably at least 70% by weight, most preferably from about 70% to about 80% by weight.

The microcrystalline cellulose may have a moisture content of up to 5.0% or a moisture content of up to 1.5%.

The pharmaceutical composition may further comprise a disintegrant. The disintegrant may be selected from the group consisting of kaolin, starch, powdered sugar, sodium starch glycolate, crosscarmelose sodium, carboxyirethyl cellulose, microcrystalline cellulose and sodium alginate. Preferably, the disintegrant is a pregelatinized starch. The starch may have a moisture content of up to 14%, preferably a moisture content of up to 12%, more preferably a moisture content of up to 7%, most preferably a moisture content of up to 5%.

The pharmaceutical composition may further comprise a lubricant. The lubricant may be selected from the group consisting of talc, sodium stearyl fumarate, magnesium stearate, calcium stearate, hydrogenated castor oil, hydrogenated soybean oil, and polyethylene glycol. Preferably, the lubricant is magnesium stearate.

The pharmaceutical composition may further comprise a protease inhibitor.

The pharmaceutical composition may further comprise an enteric coating. The enteric coating may be methacrylic ester copolymer, cellulose acetate phthalate (CAP), hydroxypropyl methyl cellulose phthalate (HPMCP), carboxymethyl ethyl cellulose (CMEC), amino-alkylmethacrylate copolymer. Preferably, the enteric coating is methacrylic acid copolymer.

The pharmaceutical composition may further comprise a film coating under the enteric coating. The film coating may be selected from the group consisting of hydroxy propyl methyl cellulose (HPMC) and poly vinyl alcohol (PVA).

The pharmaceutical composition may be in solid form. The solid form may be selected from the group consisting of a tablet, a hard gelatin capsule, a pellet and a particulate formulation.

When the pharmaceutical composition is in solid form, it may be a tablet and the effective amount of Copolymer 1 is from about 0.1 mg to about 300 mg, preferably from about 5 mg to about 100 mg. In another embodiment, the effective amount of Copolymer 1 is from about 5 mg to about 50 mg. In a preferred composition, the effective amount of Copolymer 1 is about 5 mg. In another preferred embodiment, the effective amount of Copolymer 1 is about 10 mg. In a further preferred composition, the effective amount of Copolymer 1 is about 50 mg. In one embodiment, the effective amount of Copolymer 1 (glatiramer acetate) is about 0.01 mg/kg to about 2 mg/kg. In a preferred composition, the effective amount of Copolymer 1 (glatiramer acetate) is about 0.05 mg/kg to about 1 mg/kg.

In a preferred embodiment, the pharmaceutical composition in solid form comprises as an active ingredient a therapeutically effective amount of Copolymer 1, 70%–80% by weight of microcrystalline cellulose, an enteric coating, and either 5 mg or 50 mg of Copolymer 1.

The pharmaceutical composition may further comprise a pharmaceutically acceptable carrier suitable for application to mucosal linings, so as to thereby form a composition suitable for application to the mucosal linings of a subject. Preferably, the carrier is chitosan.

The pharmaceutical composition may further comprise a pharmaceutically effective amount of an anti-microbial preservative. The anti-microbial preservative may be selected from the group consisting of sodium benzoate, methyl paraben, benzalkonium chloride, and propyl paraben.

According to this invention, the pharmaceutical composition may be in either aqueous form, or in dry powder form.

The mucosal linings to which the pharmaceutical composition may be administered may be bronchi-associated lymphoid tissue.

The pharmaceutical composition may be formulated for either oral administration, buccal administration, nasal administration, or pulmonary administration.

Also disclosed is a process for manufacturing the pharmaceutical composition, wherein the process comprises a) milling the Copolymer 1, and b) dry mixing and/or granulating the milled Copolymer 1 with at least 50% by weight of microcrystalline cellulose.

The process may further comprise applying a film coating or applying an enteric coating. The enteric coating may be applied using a rotating pan system.

Also disclosed is a method for treating an autoimmune disease in a mammal which comprises administering to the mammal the pharmaceutical composition according to this invention. The autoimmune disease is selected from the group consisting of an arthritic condition, autoimmune hemolytic anemia, autoimmune oophoritis, autoimmune uveoretinitis, Crohn's disease, chronic immune thrombocytopenic purpura, colitis, contact sensitivity disease, Graves disease, Guillain-Barre's syndrome, Hashimoto's disease, idiopathic myxedema, myasthenia gravis, psoriasis, pemphigus vulgaris, rheumatoid arthritis, GVHD or HVGD. Preferably, the autoimmune disease is multiple sclerosis.

Thus, this invention provides a method for treating autoimmune diseases by oral administration of Copolymer 1. When Copolymer 1 is introduced orally, it may be mixed with other food forms and consumed in solid, semi-solid, suspension or emulsion form; and it may be mixed with pharmaceutically acceptable carriers, including water, suspending agents, emulsifying agents, adjuvants, flavor enhancers and the like. In one embodiment, the oral composition is enterically-coated. Use of enteric coatings are well known in the art. Commonly known enteric coatings include Eudragit S and Eudragit L (K. Lehman, Acrylic Coatings in Controlled Release Tablet Manufacture, Manufacturing Chemist and Aerosol News, p. 39 (June 1973); K. Lehman, Programmed Drug Release from Oral Program Forms, Pharma. Int., vol. ISS 3 1971, p. 34–41; Handbook of Pharmaceutical Excipients, $2^{nd}$ ed.).

An additional object of the present invention is to provide forms of Copolymer 1 that can be administered nasally to treat autoimmune conditions. For instance, Copolymer 1 may be administered as dry powder or metered dose of solution by inhalation, or nose-drops and nasal sprays, using appropriate formulations and metered dosing units. These formulations are intended to deliver Copolymer 1 to either (i) mucosal linings of the lungs and associated airways or (ii) mucosal linings of the nasal cavities.

As contemplated, Copolymer 1 is brought into contact with those lymphoid tissues in the mucosal linings which are believed to be a primary source of immune system sensitization. These mucosal linings may be found (though not necessarily exclusively) in the sinuses, trachea, bronchial passages (where they are known as the BALT or bronchi-associated lymphoid tissues) and gastrointestinal linings (known as GALT or gut-associated lymphoid tissues). Thus, the administration of Copolymer 1 is understood to include methods wherein Copolymer 1 is introduced into the body by way of ingestion or inhalation. For example, Copolymer 1 may be administered by way of the mouth through feeding, through a stomach tube, by inhalation into the bronchial passages or by nasal inhalation.

The composition contemplated by the subject invention may be administered either as a simple oral solution, as an emulsion or suspension formulation, as a solid oral dosage form (capsule or tablet), or even as a soft gelatin capsule. The present invention contemplates immediate release dosage forms and modified release dosage forms (including particulates, coated granules and pellets, emulsions, microemulsions and encapsulation in microspheres and nanospheres).

Coated formulations may include enteric and non-enteric formulations. Enteric-coated dosage forms include the enteric-coated tablet, soft and hard gelatin capsule, pellet, particle and microparticle formulations. For instance, one may employ Eudragit (methacrylic acid copolymer) or Opadry (hydroxy propyl methyl cullulose ("HPMC") or poly vinyl alcohol ("PVA")) coatings, designed to target release by pH control in the stomach or in the gut, in the duodenum, jejunum, ileum or colon. Control of release may also be achieved through matrix erosion or time release formulations. Inactive ingredients can include lactose, microcrystalline cellulose, mannitol, PVP, starch, sodium starch glycolate, stearic acid, talc, hydrogenated triglycerides, polylactic acid and polyglycolic acid copolymers, or other ingredients intended specifically to enhance gut absorption.

Solid oral dosage form manufacturing processes can include direct compression and tableting, dry granulation, wet granulation, particulate and pellet manufacture by extrusion, spheronisation and melt granulation. The bulk drug substance may be mixed or milled prior to blending with other excipients, or co-dissolved and sprayed in a solution in a wet granulation process. Spray drying may also be an appropriate method to achieve therapeutically important particulate formulations with or without an inactive ingredient (such as lactose). The amount of active ingredient within the composition can be in the range of 0.01 mg to 1000 mg, while the range 0.1 mg to 300 mg is likely to be optimal.

Autoimmune diseases contemplated by the present invention include either cell-mediated disease (e.g., T cell) or antibody-mediated (e.g., B cell) disorders. Such disorders can be inter alia, arthritic conditions, demyelinating diseases and inflammatory diseases. For example, autoimmune diseases which can be treated by the present compositions include multiple sclerosis, arthritic conditions, autoimmune hemolytic anemia, autoimmune oophoritis, autoimmune uveoretinitis, Crohn's disease, chronic immune thrombocytopenic purpura, colitis, contact sensitivity disease, Graves disease, Guillain-Barre's syndrome, Hashimoto's disease, idiopathic myxedema, myasthenia gravis, psoriasis, pemphigus vulgaris, rheumatoid arthritis, and GVHD or HVGD. The present compositions can be used to treat one or more of these diseases.

The phrase, "arthritic condition", as used herein is a condition wherein at least one symptom of rheumatoid arthritis is observed in at least one joint of a mammal, for example in a shoulder, knee, hip, backbone or digit. Examples of arthritic conditions include "polyarthritis", which is an arthritic condition that affects more than a single joint; "juvenile arthritis", an arthritic condition of humans under the age of 21; and Felty's syndrome, which can include the symptoms of neutropenia, splenomegaly, weight loss, anemia, lymphadenopathy, and pigment spots on the skin. It is to be understood and expected that variations in the principles of invention herein disclosed may be made by one skilled in the art and it is intended that such modifications are to be included within the scope of the present invention.

Experimental Details

EXAMPLE 1

Production of Enteric-Coated Capsules and Tablets

Experiment 1A

Initial pre-clinical and clinical studies were performed using enteric-coated hard gelatin capsule formulations. All formulations were tested to meet (i) assay and impurities specifications, (ii) quality specifications for Copolymer 1, (iii) USP requirements for uniformity of dosage units by content uniformity and (iv) USP requirements for drug release for delayed release (enteric-coated) articles. Together, these tests were intended to ensure that each lot meets the necessary requirements for identity, strength, quality and purity.

Experimental lots of enteric-coated hard gelatin capsules were prepared for initial evaluation in monkeys suffering from EAE, manufactured using co-lyophilized Copolymer 1 and mannitol, sieved and hand-filled into hard gelatin capsules. The capsules were film-coated with Opadry (white) (commercial grades of hydroxy propyl methyl cellulose (HPMC) coating formulations marketed by Colorcon® (UK)) and then enteric-coated using methacrylic acid copolymer NF (Eudragit L-30 D-55, a commercial grade of methacrylic acid copolymer, available as a stabilized 30% aqueous dispersion, manufactured by Rohm® (Germany)) using a Wurster fluid bed dryer (Accelacota 10).

The methacrylic acid copolymer used was Eudragit L 30 D-55, which is an aqueous dispersion of a methacrylic acid and acrylic acid ethyl ester. The ratio of free carbonyl groups to ester groups is 1:1. The films dissolve above pH 5.5 forming salts with alkali, thus affording coatings which are insoluble in gastric media, but soluble in the small intestine.

Table 1 lists the inactive ingredients employed in the hard gelatin capsules and the purpose of each component. Capsules containing 1 mg and 20 mg of active ingredient were developed.

TABLE 1

Excipients in Hard Gelatin Capsule Formulations

| Inactive Ingredient | Pharmaceutical Function |
|---|---|
| Powder-Fill | |
| Lactose Monohydrate NF | Filler |
| Silicon Dioxide NF | Glidant |
| Pregelatinized Starch NF | Disintegrant |
| Magnesium Stearate NF | Lubricant |
| Film-Coating Suspension | |
| Opadry YS-1-7006 (clear) | Film coating |
| Purified Water USP | Coating suspension solvent* |
| Enteric-Coating Suspension | |
| Methacrylic Acid Copolymer NF (Eudragit L-30 D-55) | Enteric-coating |
| Talc USP | Glidant |
| Triethyl Citrate NF | Plasticizer |
| Purified Water USP | Coating suspension solvent* |

*Coating solvent evaporated to dryness i) Composition

TABLE 2

| Components | Composition (mg/capsule) | |
|---|---|---|
| Strength | 1 mg | 20 mg |
| Powder Fill | | |
| Copolymer 1 | 1.0 | 20.0 |
| Mannitol USP | 48.8 | 17.5 |
| Seal coat | | |
| Opadry (S-OY-7399) white | 32.7 | 32.7 |
| Purified Water USP | * | * |
| Enteric Coat | | |
| Merthacrylic acid copolymer NF (Eudragit L30 D-55) | 20.3 | 20.3 |
| Talc USP | 10.3 | 10.3 |
| Triethyl citrate NF | 2.1 | 2.1 |
| Purified Water USP | * | * |

* Processing solvent evaporated to dryness.

(ii) Manufacturing Process

1. Compounding of solution of 1.2 L of Copolymer 1 and mannitol in water
2. Lyophilization in bulk in Edward's lyoflex 0.5 pilot lyophilizer
3. Sieving—mesh #20/mesh#50.
4. Capsule filing—semi-manual Feton capsule filing machine.
5. Film coating Opadry (S-OY-7399 white) in Würster fluid bed dryer.
6. Enteric coating (Eudragit L30 D55 spraying suspension) in Würster fluid bed dryer.

Rhesus monkeys were fed with the enteric coated capsules. 5 feedings before disease induction and 5 feedings after disease induction, on alternate days. Experimental allergic Encephalomyelitis (EAE) was induced by injecting 8 mg myelin basic protein (MBP) in complete Freund's adjuvant (CFA) intra-dermally into the leg. EAE symptoms were evaluated on the following scale:

Evaluation of EAE clinical signs

| Score | Clinical State |
|---|---|
| 0 | Normal neurological exam and appearance |
| 1 | Weight loss, anorexia, yawning, slow responses to stimuli, irritability or lethargy |
| 2 | Mild neurological signs, indifference, drooling, clumsiness using limbs, ataxia, tremor, altered cry and disordered gaze |
| 3 | Moderate neurological signs, blindness (pupils do not react to light), akinesia, leg weakness or paralysis |
| 4 | Severe neurological signs, semicoma, coma, quadriplegia. When the animal reached a score of 4 it was sacrificed for humane reasons |
| 5 | Death |

As can be seen in FIG. 1, control animals developed EAE on day 25 post disease induction and died within 4 days from the disease.

Animals that were fed with 20 mg Copolymer 1 in enteric coated capsules did not develop any signs of disease till day 60, when it was sacrificed for histology. One animal per group was used.

The animal that was treated with 1 mg Copolymer 1 in enteric coated capsules developed some signs of disease (score 2+), but upon treatment with 20 mg capsules healed completely.

Figure 2:
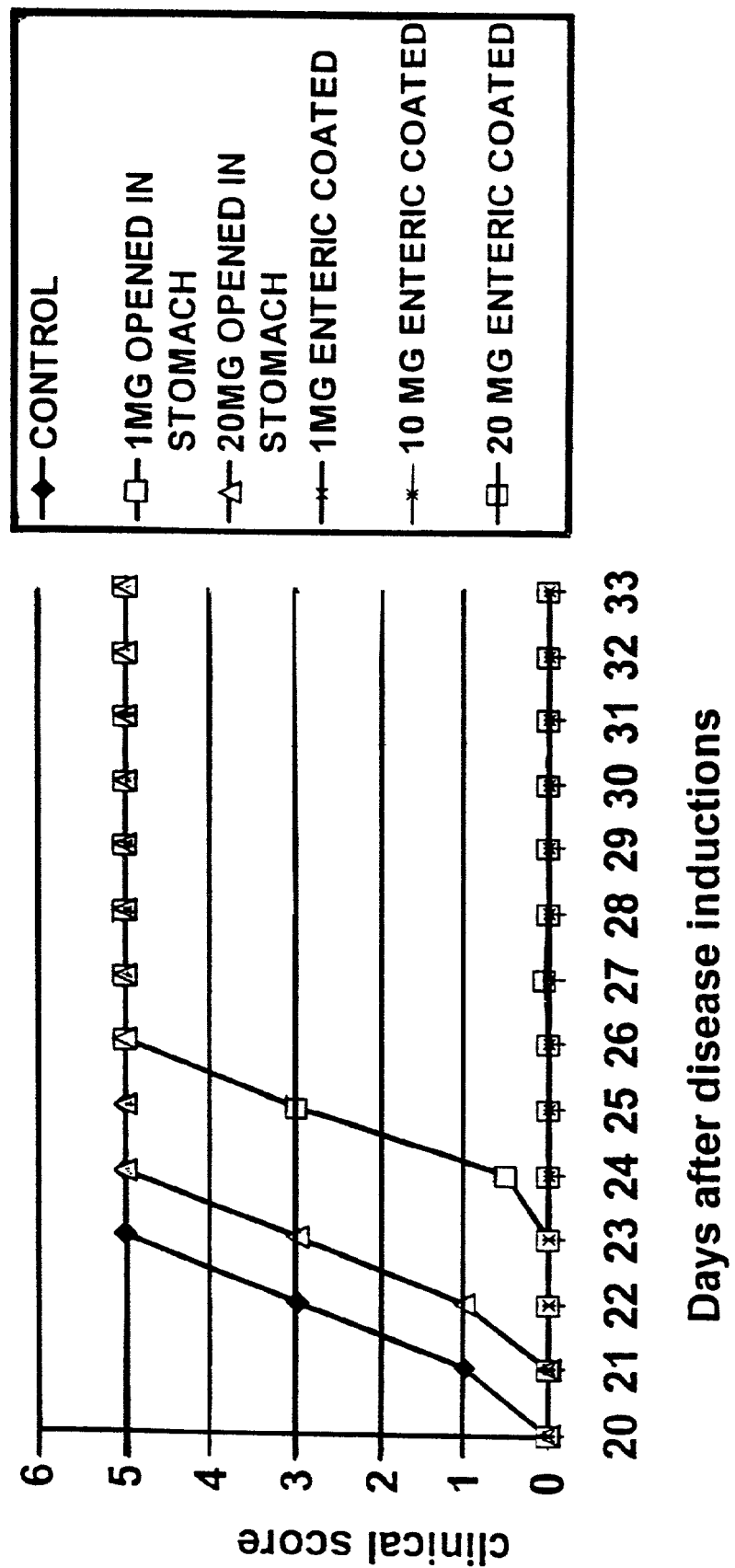
FIG. 2 shows prevention of EAE in Rhesus monkeys fed with Copolymer 1 enteric coated capsules.

In a second study (FIG. 2), all monkeys treated with Copolymer 1 enteric coated capsules (1, 10, and 20 mg) were fully protected from EAE while monkeys treated with Copolymer 1 in capsules which were not gastro-protective (opened in the stomach) or control capsule died from the disease, indicating the importance of the enteric coating in these dose levels (1 to 20 mg.).

Experiment 1B

The procedure of Experiment 1A was adapted to give a stable product under refrigerated conditions that (i) can be manufactured using standard industrial pharmaceutical processes and (ii) meets pre-defined quality specifications appropriate for initial clinical evaluation. Here, the previous experiment's process of manufacturing the powder-fill was replaced by a dry granulation process.

(i) Composition

TABLE 3

| Components | composition mg/capsule | | |
|---|---|---|---|
| Strength | Placebo | 20 mg | 100 mg |
| Powder Fill | | | |
| Copolymer 1 | 0.0 | 20.0 | 100.0 |
| Lactose monohydrate NF | 322.7 | 36.6 | 183.2 |
| Pregelatinized starch NF | 37.3 | 6.7 | 33.3 |
| Silicon Dioxide NF | 9.3 | 1.7 | 8.3 |
| Magnesium Stearate NF | 3.7 | 0.7 | 3.3 |
| Seal Coat | | | |
| Opadry (YS-1-7006 clear) | 29.0 | 29.0 | 29.0 |
| Purified Water USP | * | * | * |
| Enteric Coat | | | |
| Methacrylic acid copolymer NF (Eudragit L30 D55) | 50.6 | 50.6 | 50.6 |
| Talc USP | 25.4 | 25.4 | 25.4 |
| Triethyl citrate NF | 8.0 | 8.0 | 8.0 |
| Purified Water USP | * | * | * |

* Processing solvent evaporated to dryness.

(ii) Manufacturing process (6 kg)
1. Milling of Copolymer 1—(fitzmill milling machine)
2. Blending with excipients—Y-cone 15 blender
3. Compression of slugs (20 mm, 1 g)—Killian tableting machine
4. Granulation of slugs—Frevitt granulator, 0.8 mm net
5. Blending with excipients—Y-cone 15 blender
6. Capsule filling—Bosch 400 encapsulator.
7. Coating (Accelacota -10 rotating pan machine).

The clinical formulation was administered to patients suffering from multiple sclerosis (MS) in the framework of the Phase I study. It was demonstrated that Copolymer 1 (20, 100 and 300 mg.) in enteric coated capsules was tolerated and safe in MS patients.

In addition, oral administration of Copolymer 1 in enteric coated capsules modified the cytokine profile in multiple sclerosis patients (increase of IL-10 and decrease in IL-2) indicating a possible clinical effect of this formulation in MS patients.

Experiment 1C

Enteric-coated tablets (7.0 mm, round, 20 mg active ingredient) were chosen for further toxicological evaluation in monkeys. To create a stable product at controlled room temperature, Experiment 1B's procedure was modified. The lactose monohydrate filler used in the capsule formulations was replaced with microcrystalline cellulose NF (Avicel PH 102) due to the observation of long-term incompatibility with the active ingredient (a Maillard reaction occurred under accelerated storage conditions that resulted in yellowing of the granulate inside the capsule). Sodium starch glycolate NF was employed as the disintegrant; the slightly more rapid drug release brought about by sodium starch glycolate NF assisted in the toxicological evaluation in monkeys, where the gut is shorter than in humans.

A different opadry grade (Y-1-7000H) was used, even though this is also hydroxy propyl methyl cellulose ("HPMC")-based.

A corresponding placebo formulation was also developed.

The microcrystalline cellulose used was Avicel® PH 102, although Avicel® PH 101, and Avicel® PH 112, all manufactured by FMC Corporation, could be used. Microcrystalline cellulose fillers were employed in the experiments for tablet formulation. The three different kinds of microcrystalline cellulose binders mentioned differ in moisture content. Avicel® PH 101 and Avicel® PH 102 are both high moisture content microcrystalline cellulose binders having less than or equal to 5% moisture content. Avicel® PH 112 is a low moisture content microcrystalline cellulose binder having less than or equal to 1.5% moisture content. The mean particle size of Avicel® ranges from 20 to 200 microns. The mean particle size of Avicel® PH 102 is 100 microns.

(i) Composition

TABLE 4

| | Amount (mg)/Tablet | |
|---|---|---|
| Ingredients | 0 mg | 20 mg |
| Tablet Core | | |
| Copolymer 1 | 0.0 | 20.0 |
| Microcrystalline cellulose NF | 105.2 | 71.5 |
| Silicon dioxide NF | 2.9 | 2.5 |
| Sodium starch glycolate NF | 5.8 | 5.0 |
| Magnesium stearate NF | 1.1 | 1.0 |
| Enteric Coat | | |
| Methacrylic acid copolymer NF (Eudragit L-30 D-55) | 9.4 | 9.4 |
| Talc USP | 4.7 | 4.7 |
| Triethyl citrate NF | 0.9 | 0.9 |
| Purified water USP | * | * |
| Total coating weight per tablet | 15.0 | 15.0 |
| Final coated tablet weight | 130.0 | 115.0 |

* Processing solvent evaporated to dryness.

(ii) Manufacturing Process (6 kg)
1. Milling of Copolymer 1 —(fitzmill milling machine)
2. Blending with excipients—Y-cone 15 blender
3. Compression of slugs (20 mm, 1 g)—Killian tableting machine
4. Granulation of slugs—Frevitt granulator, 0.8 mm net
5. Blending with excipients—Y-cone 15 blender
6. Tableting—Killian tableting machine.
7. Coating (Accelacota-10 rotating pan machine).

Experiment 1D

Experiment 1C's procedure was adapted to create similar formulations of enteric-coated tablets for clinical evaluation in humans suffering from multiple sclerosis. Pregelatinized starch was employed as the disintegrant. Tablet shape and size were selected as appropriate for enteric administration and found to be suitable for the intended pharmaceutical manufacturing processes, including coating. The 5 mg active ingredient tablets (and corresponding placebos) were manufactured in the same shape and size as in Experiment 1C. The size and shape of the 50 mg active ingredient tablets (and corresponding placebos) was changed into 14.7 mm×8.1 mm oval-shaped tablets appropriate for enteric administration and the intended pharmaceutical manufacturing processes, including coating.

Scale-up and process qualification studies were completed for 52 kg lots of tablet cores for both the 5 mg and 50 mg active ingredient. The tablet cores' composition is presented below.

(i) Composition of Tablet Cores

TABLE 5

| | amounts of active ingredient (mg/tablet) | | | |
|---|---|---|---|---|
| Ingredients | 0 mg | 0 mg | 5 mg | 50 mg |
| Tablet Core | | | | |
| Copolymer 1 | 0.0 | 0.0 | 5.0 | 50.0 |
| Microcrystalline cellulose NF (Avicel PH 102) | 105.2 | 366.0 | 86.5 | 316.0 |
| Silicon dioxide NF | 2.9 | 10.0 | 2.5 | 10.0 |
| Pregelatinized starch NF | 5.8 | 20.0 | 5.0 | 20.0 |
| Magnesium stearate NF | 1.1 | 4.0 | 1.0 | 4.0 |
| Total | 115.0 | 400.0 | 100.0 | 400.0 |
| Enteric Coat | | | | |
| Methlacrylic acid copolymer NF (Eudragit L-30 D-55) | 9.4 | 21.9 | 9.4 | 21.9 |
| Talc USP | 4.7 | 11.0 | 4.7 | 11.0 |
| Triethyl citrate NF | 0.9 | 2.1 | 0.9 | 2.1 |
| Purified water USP | * | * | * | * |
| Total coating weight per tablet | 15.0 | 35.0 | 15.0 | 35.0 |
| Final coated tablet weight | 130.0 | 435.0 | 115.0 | 435.0 |

* Processing solvent evaporated to dryness.

(ii) Manufacturing process (52 kg)
1. Milling of Copolymer 1—(fitzmill milling machine)
2. Blending with excipients—Y-cone 120 blender
3. Compression of slugs (20 mm, 1 g)—Killian tableting machine
4. Granulation of slugs—Frevitt granulator, 0.8 mm net
5. Blending with excipients—Y-cone 120 blender
6. Tableting—Killian tableting machine.
7. Coating sub-lots (Accelacota-10 rotating pan machine).
Accelerated stability testing (at 40° C./75% Relative Humidity) of lots with
(i) different film-coating Opadry formulations; and
(ii) different slug hardness values indicated that optimal formulations can be achieved by carefully controlling slug hardness and using L30 D55 Eudragit with or without Opadry film coat (or any other hydroxy propyl methyl cellulose (HPMC) formulation).

Figure 3:
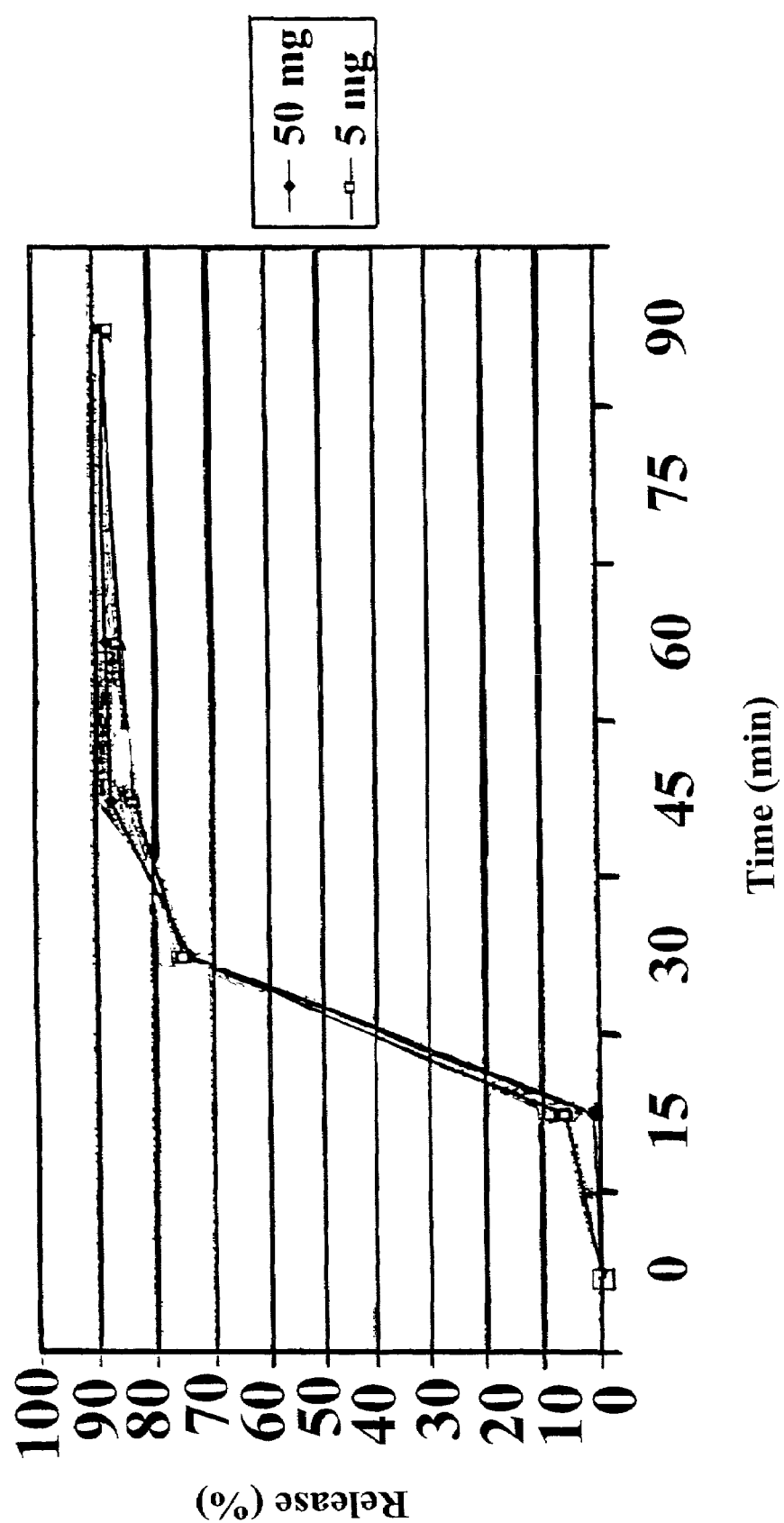
FIG. 3 shows the drug release profile of Copolymer 1 enteric-coated tablets.

The dissolution profiles of the 5 mg and the 50 mg tablets were compared and found to be matching despite the four-fold difference in tablet weight. The dissolution profiles (in buffer at pH 6.8) are shown in FIG. 3.

Example 2

Oral Administration of Copolymer 1 Solution

Example 2A

Gavage Administration of Copolymer 1 in Solution to Rats

EAE was induced in Lewis rats by the injection of guinea pig spinal cord homogenate in CFA into the hind legs.

For EAE suppression, rats were fed with Copolymer 1 solution (0.1–10 mg/kg.) every day, starting from the day of EAE induction, up to day 24 (test termination).

Figure 4:
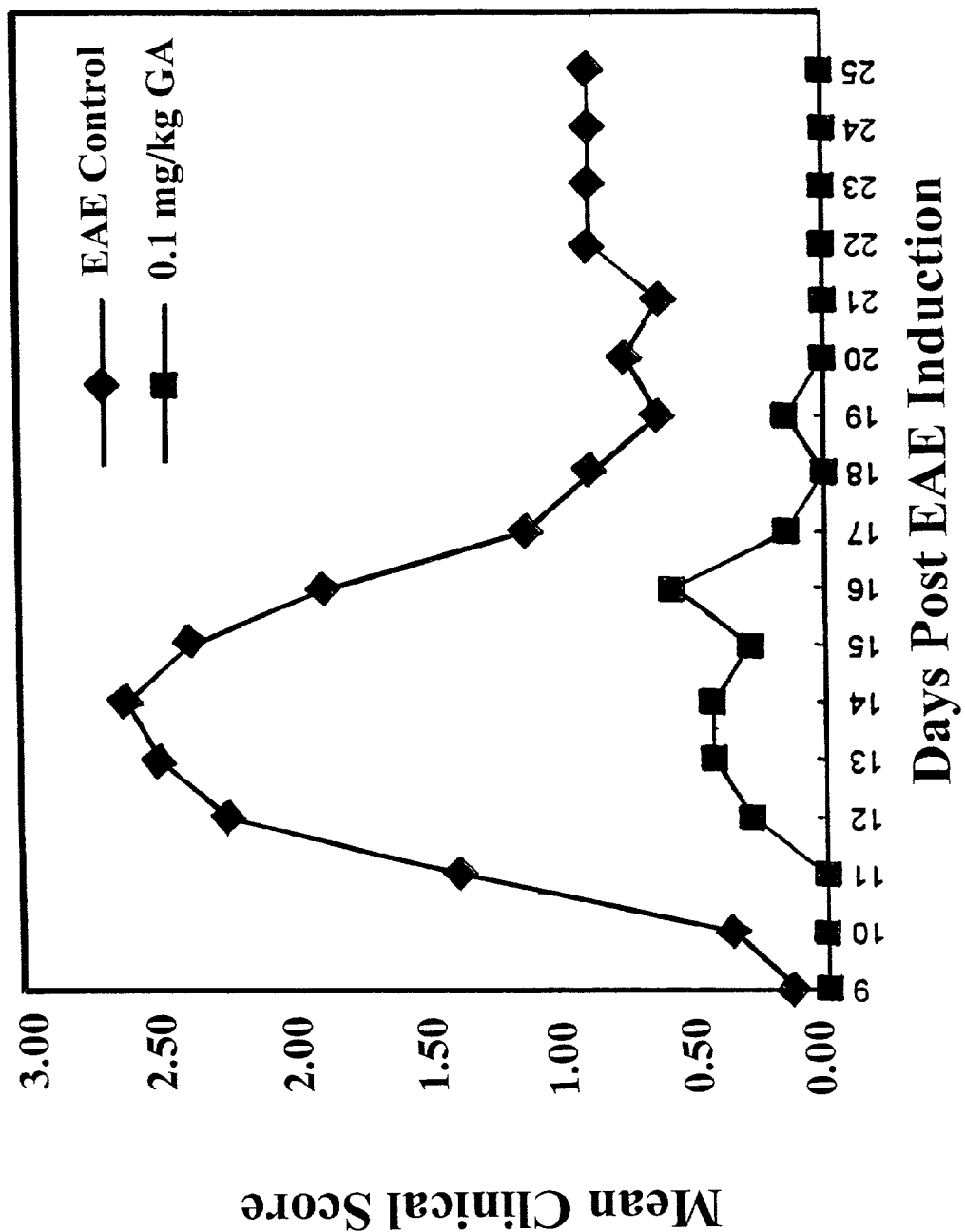
FIG. 4 shows the effect of daily oral Gavage treatment with Copolymer 1 solution on rat EAE.

Copolymer 1 inhibited EAE at all tested doses, with bimodal dose response pattern. The most effective doses were the lowest dose 0.1 mg/kg (see FIG. 4) and the highest dose of 10 mg/kg.

In all groups, Copolymer 1 delayed disease onset, reduced the % of sick rats, the severity of disease (as expressed by the mean score and the mean maximal score) and the disease duration.

Example 2B

Suppression of Chronic-Relapsing EAE in Biozzi Mice by Oral Administration of Copolymer 1 in Solution The chronic—relapsing EAE model represents MS better due to its relapsing nature. It enables the demonstration of drug effect on a disease which is on-going, similar to the situation of treating the human disease, which is on-going.

Chronic—relapsing EAE was induced in female Biozzi mice by the injection of mouse spinal cord homogenate (MSCH) in CFA, following by re-injection of the encephalitogen one week later, in the same manner.

On day 16 when the mice were already sick (see FIG. 5), they were randomized into 4 groups and treated daily by either phosphate buffer saline (PBS) as control or with Copolymer 1 solution (0.5 mg/kg/day, 2.5 mg/kg/day and 12.5 mg/kg/day).

Figure 5:
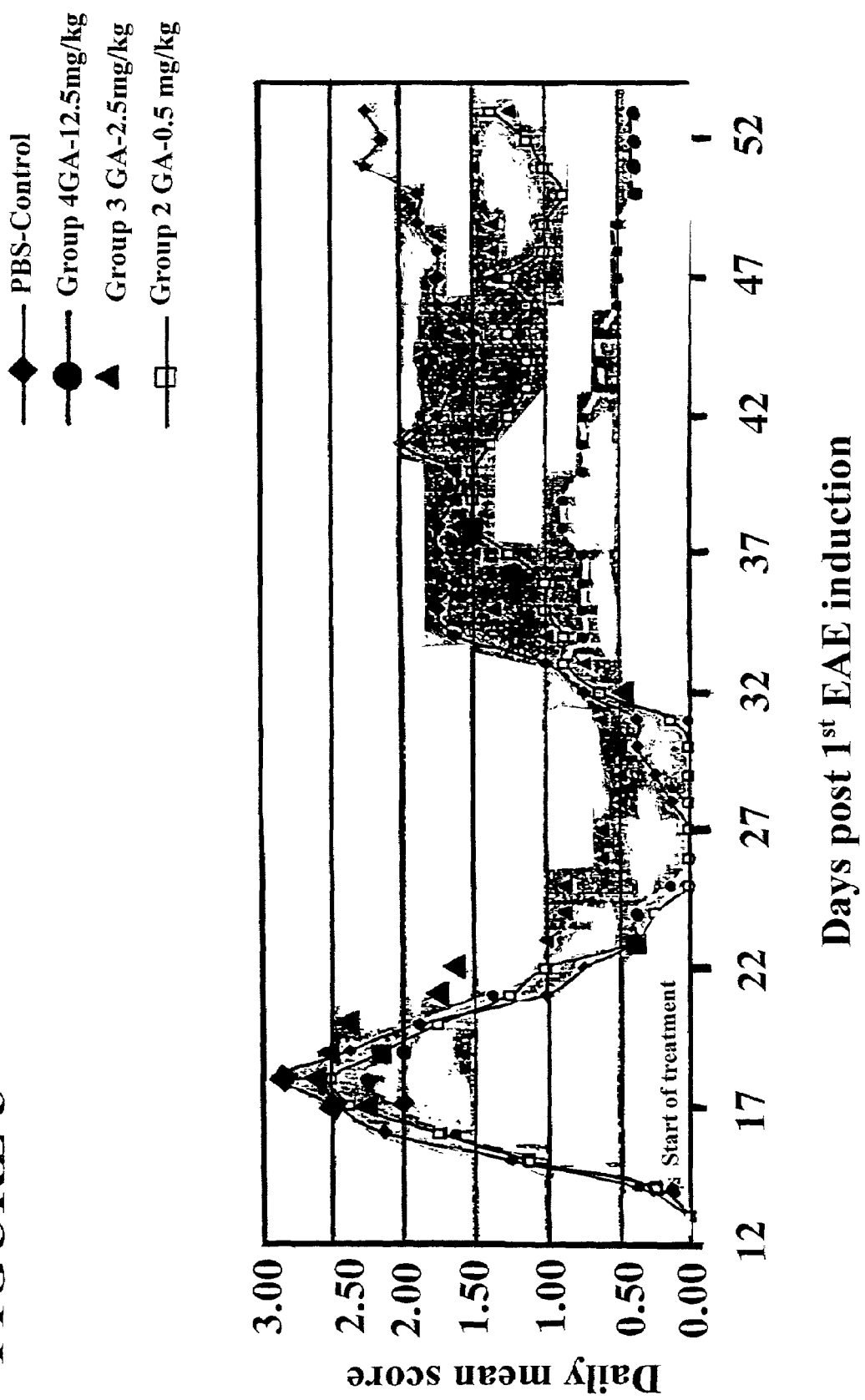
FIG. 5 shows the results of treatment of chronic-relapsing (CR)-EAE in Biozzi mice with oral Copolymer 1 solution.

As can be seen in FIG. 5, treatment with Copolymer 1 reduced the EAE clinical symptoms of the second relapse in a dose-dependent manner. The most effective dose was 12.5 mg/kg. The suppressive effect was demonstrated in all parameters checked: the incidence of mice suffering from second relapse, the severity of symptoms and the duration of the relapse.

Example 3

Oral Administration of Copolymer 1 Tablets

Example 3A

Induction of Relapsing-Remitting EAE in Cynamologus Monkeys

A relapsing-remitting form of EAE was induced by the injection of emulsified MBP in CFA containing 3 mg/ml of Mycobacterium Tuberculosis (MT), intradermally into right & left footpads.

The daily dosages employed are presented in Table 6 below. Observation was initiated on day 8. Local reaction was observed at the site of injection, an ulcer/or bleeding ulcer caused intermittent use of the foot and/or flexion of the toes. Neurological signs appeared on day 14 following induction, as shown in Table 6.

TABLE 6

| Monkey I.D. | Dose | Daily Clinical Score DAYS | | | | | |
|---|---|---|---|---|---|---|---|
| | | 14 | 15 | 16 | 17 | 18 | 19–32 |
| Female Z-920 | 2.5 mg | 3 | 3 | 5 | | | |
| Female Z-929 | 5 mg | 0 | 0 | 3 | 4* | | |
| Female Z-485 | 10 mg | 1 | 2 | 3 | 5 | | |
| Male Z-523 | 2.5 mg | 0 | 2 | 3 | 3/4 | 4* | |
| Male Z-1669 | 5 mg | 0 | 0 | 0 | 0 | 0 | 0 |
| Male Z-701 | 10 mg | 0 | 0 | 0 | 0 | 0 | 0 |

*euthanized

Table 6 demonstrates that the appearance of EAE was acute, (grade 3). Two of the females died within 48 hours of onset of signs of EAE, whereas the third female was euthanized subsequent to the development of grade 4 signs (coma).

Only one male developed signs of EAE and was euthanized after it reached grade 4. The two males which did not develop signs of EAE were euthanized after 32 days.

Thus, the dose injected for the induction of EAE does not relate to the time interval between injection and appearance of signs of EAE, or the severity of signs. The females were the first to develop the signs of EAE, and the first to die. Only a third of the males developed EAE.

Example 3B

Treatment of EAE in Cynamologus Monkeys by Oral Administration of Copolymer 1 in Enteric-Coated Tablets Twelve Cynomologus monkeys weighing 3 to 4 kg at the age of approximately four years were randomly divided into four treatment groups. For 10 days on every alternate day (total of 5 treatments), each monkey was introduced with the tablets using tip coated forceps beyond the radix of the tongue, after which swallowing was assured. The groups were treated as follows:
 Group #1 (placebo control): four placebo tablets
 Group #2 (5 mg Copolymer 1 per treatment): one tablet of 5 mg Copolymer 1 and 3 placebo tablets
 Group #3 (10 mg Copolymer 1 per treatment): two tablets of 5 mg Copolymer 1 and 2 placebo tablets
 Group #4 (20 mg Copolymer 1 per treatment): four tablets of 5 mg Copolymer 1.

Subsequently, following the procedure of Example 3A, EAE was induced in all monkeys by single injection with 2.5 mg of MBP per monkey. Simultaneously, each group began daily treatment with the same dose of Copolymer 1 as they received prior to the induction of EAE for 30 days.

In the first study, Cop-1 treatment continued until day 52. In the second study, Cop-1 treatment continued until day 57. MBP was administered in a single administration. Cop-1 was administered continuously except for several weekends in the first study, and except for Saturdays in the second study.

The monkeys were examined every Sunday to Friday, and also not monitored on Saturdays, starting from day 8 after disease induction until day 52. At the end of this period, the monkeys were sacrificed and the tissue was harvested. Local reaction was observed at the site of injection, such as an ulcer and/or bleeding ulcer, which caused intermittent use of the foot and/or flexion of the toes. EAE-related neurological signs appeared between day 12 and 20 following induction, as specified in Table 7 below.

TABLE 7

| DOSE | | 0 mg | 0 mg | 0 mg | 5 mg | 5 mg | 5 mg | 10 mg | 10 mg | 10 mg | 20 mg | 20 mg | 20 mg |
|---|---|---|---|---|---|---|---|---|---|---|---|---|---|
| MONKEY ID | | 607 | 623 | 427 | 540 | 495 | 662 | 1652 | 1654 | 493 | 453 | 484 | 482 |
| DAYS | 12 | 0 | 0 | 0 | 0 | 0 | 0 | 0 | 0 | 0 | 0 | 0 | 2 |
| | 13 | 0 | 0 | 0 | 0 | 0 | 0 | 0 | 0 | 0 | 0 | 0 | 3 |
| | 14 | 0 | 0 | 0 | 0 | 0 | 0 | 0 | 0 | 0 | 0 | 0 | **4 |
| | 15 | 0 | 0 | 0 | 0 | 0 | 1 | 0 | 0 | 0 | 0 | 2 | 4 |
| | 16 | 0 | 0 | 0/1 | 0 | 0 | 2 | 0 | 0 | 0 | 0/1 | 3 | 4 |
| | 17 | 1 | 2 | 0/1 | 0 | 0 | 2 | 0 | 0 | 0 | 0/1 | ***5 | 4 |
| | 18 | 0 | 2 | 0/1 | 0 | 0 | 3 | 0 | 0 | 0 | 0 | 5 | 4 |
| | 19 | 0 | 2 | 0/1 | 0 | 0/1 | 3 | 2 | 0 | 0 | 0 | 5 | 4 |
| | 20 | 2 | 2 | 1 | 0/1 | 0/1 | 3 | 2 | 0/1 | 0 | 0/1 | 5 | 4 |
| | 21 | 2 | 2 | 1 | 0/1 | 1 | 3 | 2 | 0/1 | 0 | 1 | 5 | 4 |
| | 22 | 2 | 2 | 1 | 0/1 | 0 | 3 | 2 | 0 | 0 | 0/1 | 5 | 4 |
| | 23 | 2 | 2 | 1 | 0/1 | 0/1 | 3 | 2 | 0/1 | 0 | 0 | 5 | 4 |
| | 24 | 1 | 0 | 0 | 0 | 0 | 2 | 0 | 0 | 0 | 2 | 5 | 4 |
| | 25 | 1 | 0 | 0 | 0 | 0 | 2 | 0 | 0 | 0 | 1 | 5 | 4 |
| | 26 | 0 | 0 | 0 | 0 | 0 | 2 | 0 | 0 | 0 | *1 | 5 | 4 |
| | 27 | 0 | 0 | 0 | 0 | 0 | 2 | 2 | 0 | 2 | *1 | 5 | 4 |
| | 28 | 0 | 0 | 0 | 0 | 0 | 2 | 2 | 0 | 0 | *1 | 5 | 4 |
| | 29 | 0 | 0 | 0 | 0 | 0 | 2 | 2 | 0 | 0 | *1 | 5 | 4 |

TABLE 7-continued

Daily Clinical Score.

| DOSE<br>MONKEY ID | | 0 mg<br>607 | 0 mg<br>623 | 0 mg<br>427 | 5 mg<br>540 | 5 mg<br>495 | 5 mg<br>662 | 10 mg<br>1652 | 10 mg<br>1654 | 10 mg<br>493 | 20 mg<br>453 | 20 mg<br>484 | 20 mg<br>482 |
|---|---|---|---|---|---|---|---|---|---|---|---|---|---|
| | 30 | 0 | 0 | 0/1 | 0 | 2 | **4 | 0/1 | 0 | 0/1 | *1 | 5 | 4 |
| | 31 | | | | | | | | | | | | |
| | 32 | 2 | 0 | 0/1 | 0/1 | 2 | 4 | 0/1 | 0 | 0 | *1 | 5 | 4 |
| | 33 | 3 | 0 | 0/1 | 0/1 | 2 | 4 | 0/1 | 0 | 0 | *1 | 5 | 4 |
| | 34 | | | | | | | | | | | | |
| | 35 | 3 | 0 | 1 | 0/1 | 2 | 4 | 2 | 0 | 0 | *1 | 5 | 4 |
| | 36 | 3 | 0 | 1 | 1 | 2 | 4 | 2 | 0 | 0 | *1 | 5 | 4 |
| | 37 | | | | | | | | | | | | |
| | 38 | **4 | 0 | 1 | 1 | 1 | 4 | 2 | 0 | 0 | *1 | 5 | 4 |
| | 39 | 4 | 0 | 1 | 1 | 2 | 4 | 2 | 0 | 0 | *1 | 5 | 4 |
| | 40 | | | | | | | | | | | | |
| | 41 | | | | | | | | | | | | |
| | 42 | 4 | 2 | 2 | 0 | 0 | 4 | 2 | 0 | 0 | *1 | 5 | 4 |
| | 43 | | | | | | | | | | | | |
| | 44 | | | | | | | | | | | | |
| | 45 | 4 | 2 | 3 | 0 | 0 | 4 | 2/3 | 0 | 0 | *1 | 5 | 4 |
| | 46 | 4 | 2 | 3 | 0/1 | 0 | 4 | 2 | 0 | 0 | *1 | 5 | 4 |
| | 47 | 4 | 2 | 3 | 1 | 0 | 4 | 2 | 0 | 0 | *1 | 5 | 4 |
| | 48 | 4 | 2 | 2 | 1 | 0/1 | 4 | 2 | 0 | 0 | *1 | 5 | 4 |
| | 49 | 4 | 2 | 2 | 1 | 0 | 4 | 2 | 0 | 0 | *1 | 5 | 4 |
| | 50 | | | | | | | | | | | | |
| | 51 | 4 | 2 | 2 | 1 | 0 | 4 | 2 | 0 | 0 | *1 | 5 | 4 |
| | 52 | 4 | 2 | 2 | 1 | 0 | 4 | 2 | 0 | 0 | *1 | 5 | 4 |

*The monkey was sacrificed for reasons not related to neurological scoring.
**The monkey was sacrificed when it reached grade 4.
***The monkey was found dead in the cage.

All three females in the placebo group showed signs of illness on days 17–23 followed by a remission period of a week. Female No. 607 had a second acute relapse on day 32 and was sacrificed on day 38 when score 4 was reached. Females No. 623 and 427 showed severe signs of illness in the last 10 days of follow up (scores 2 and 3).

In the 5 mg Copolymer 1 treatment group, Female No. 662 showed signs of illness on day 15 and by day 18, after losing her pupillary reflex, received score 3. On day 30, the animal was sacrificed after it reached score 4. The two other females, No. 540 and 495, had a similar sequence of symptoms, with mild signs on day 18/19 to day 23 (score 1) and a relapse between day 30/32 and day 39 (score 1–2). Female No. 540 had a third relapse between day 46 to day 52 (score 1).

In the group that was treated with 10 mg Copolymer 1, Female No. 1652 showed neurological symptoms from day 19 (score 2), with a short remission period between days 24–26 and 30–33(score 0/1) and survived to the end of the follow up period. Females No. 493 and 1654 showed irregular, very mild symptoms during the entire follow up period (score fluctuated between 0 and 0/1).

In the 20 mg Copolymer 1 treatment group, Females No. 482 and 484 showed a very acute onset of signs. Female No. 482 reached score 2 on day 12, 3 on day 13 and was euthanized on day 14 (score 4).

Female No. 484 registered score 2 on day 15, reached score 3 the following day and was found dead on day 17 (score 5). Female No. 453 had mild neurological symptoms, but because of suppurative infected inguinal lymph nodes and infected bleeding wounds of the foot pad, which caused the animal severe deterioration, the animal was sacrificed on day 26.

Seven females survived to the end of the follow up period and were sacrificed on day 53. Inguinal lymph nodes and sections of the intestine were harvested for immunochemical staining.

The results of this example are summarized in Table 8 below.

TABLE 8

Evaluation of Clinical Manifestations

| Treatment<br>Group | Incidence | Mean<br>Score | Mean<br>Maximal<br>Score | No.<br>Relapses* | Mean<br>Disease<br>Onset Day |
|---|---|---|---|---|---|
| Control | 3/3 | 1.27 | 3.00 | 3 (6) | 16.66 |
| 5 mg | 3/3 | 1.30 | 2.33 | 2 (5) | 18.33 |
| 10 mg | 1/3 | 0.49 | 1.33 | 1 (3) | 23 |
| 20 mg | 3/3 | 3.04 | 3.67 | 0 (3) | 14.33 |

In summary, the course of EAE was phasic, with recurrence of symptoms and remission periods. While the placebo group showed the chronic phasic pattern of the disease, leading to deterioration with time, the 20 mg Copolymer 1 treatment group had an acute onset of symptoms with a fulminate course of the disease and death. The group treated with 5 mg Copolymer 1 exhibited a pattern of disease similar to the placebo group with no obvious improvement. In the 10 mg Copolymer 1 group, two females showed irregular, very mild symptoms, while only one female showed more than very mild symptoms (score 2 with periods of remission to score 0/1). All three survived through the whole study. The difference among the placebo, 10 mg Copolymer 1 treatment group and 20 mg treatment Copolymer 1 group is significant ($p<0.0001$). However, the difference between the placebo group and the 5 mg group is not significant (n.s.) (p=n.s.).

These results suggest that the most effective dosage is 10 mg Copolymer 1.

Example 3C

Treatment of EAE in Cynamologus Monkeys by Oral Administration of Copolymer 1 in Enteric-Coated Tablets The procedure of Example 3B was followed with the following exceptions—there was no 5 mg Copolymer 1 treatment group and the monkeys were observed until day 57 after disease induction.

As in Example 3B, observation began on day 8 and continued until the conclusion of the experiment, which, in this case, was day 57. Local reaction was observed at the site of injection, such as an ulcer and/or bleeding ulcer, which caused intermittent use of the foot and/or flexion of the toes. EAE-related neurological signs appeared between day 14 and 54 as specified in Table 9. Animals were sacrificed when they reached score 4.

In the group that received the placebo, two females showed signs of illness on day 14 (scores 2 and 3). Female No. 895 was found dead on day 15 (score 5) and Female No. 171 was sacrificed on day 32 when score 4 was reached. Female No. 203 showed only mild signs of illness (score 1) on days 23–46.

In the 10 mg Copolymer 1 treatment group, Female No. 268 showed mild signs of illness on day 37, which continued until the end of the follow up period. Female No. 307 had a similar onset of symptoms, with mild signs on day 39 (score 1) but reached score 2 on days 40–46, and score 3 from day 46 until the end of the follow up period. Female No. 318 showed signs of illness (score 1) on day 14, reached score 2 on days 15–16, and score 3 on days 18–32, with an improvement starting on day 33 (score 2) until the end of the follow up period. Overall, she exhibited very mild symptoms during the entire follow up period.

TABLE 9

Daily Clinical Score.

| DOSE MONKEY ID | | 0 mg 171 | 0 mg 203 | 0 mg 895 | 10 mg 268 | 10 mg 318 | 10 mg 307 | 20 mg 285 | 20 mg 793 | 20 mg 494 |
|---|---|---|---|---|---|---|---|---|---|---|
| DAYS | 13 | 0 | 0 | 0 | 0 | 0 | 0 | 0 | 0 | 0 |
| | 14 | 2 | 0 | 3 | 0 | 1 | 0 | 0 | 0 | 0 |
| | 15 | 2 | 0 | 5 | 0 | 2 | 0 | 0 | 0 | 0 |
| | 16 | 2 | 0 | 5 | 0 | 2 | 0 | 2 | 0 | 0 |
| | 17 | | | | | | | | | |
| | 18 | 3 | 0 | 5 | 0 | 3 | 0 | 4 | 0 | 0 |
| | 19 | 3 | 0 | 5 | 0 | 3 | 0 | 4 | 0 | 0 |
| | 20 | 3 | 0 | 5 | 0 | 3 | 0 | 4 | 0 | 1 |
| | 21 | 2 | 0 | 5 | 0 | 3 | 0 | 4 | 0 | 1 |
| | 22 | 2 | 0 | 5 | 0 | 3 | 0 | 4 | 0 | 1 |
| | 23 | 2 | 1 | 5 | 0 | 3 | 0 | 4 | 0 | 1 |
| | 24 | | | | | | | | | |
| | 25 | 2 | 1 | 5 | 0 | 3 | 0 | 4 | 0 | 1 |
| | 26 | 2 | 1 | 5 | 0 | 3 | 0 | 4 | 0 | 1 |
| | 27 | 3 | 1 | 5 | 0 | 3 | 0 | 4 | 0 | 1 |
| | 28 | 3 | 1 | 5 | 0 | 3 | 0 | 4 | 0 | 1 |
| | 29 | 3 | 1 | 5 | 0 | 3 | 0 | 4 | 0 | 1 |
| | 30 | 3 | 1 | 5 | 0 | 3 | 0 | 4 | 0 | 1 |
| | 31 | | | | | | | | | |
| | 32 | 4 | 1 | 5 | 0 | 3 | 0 | 4 | 0 | 1 |
| | 33 | 4 | 1 | 5 | 0 | 2 | 0 | 4 | 0 | 1 |
| | 34 | 4 | 1 | 5 | 0 | 2 | 0 | 4 | 0 | 1 |
| | 35 | 4 | 1 | 5 | 0 | 2 | 0 | 4 | 0 | 1 |
| | 36 | 4 | 1 | 5 | 0 | 2 | 0 | 4 | 0 | 1 |
| | 37 | 4 | 1 | 5 | 1 | 2 | 0 | 4 | 0 | 2 |
| | 38 | | | | | | | | | |
| | 39 | 4 | 1 | 5 | 1 | 2 | 1 | 4 | 0 | 2 |
| | 40 | 4 | 1 | 5 | 1 | 2 | 2 | 4 | 0 | 2 |
| | 41 | 4 | 1 | 5 | 1 | 2 | 2 | 4 | 0 | 2 |
| | 42 | 4 | 1 | 5 | 1 | 2 | 2 | 4 | 0 | 2 |
| | 43 | 4 | 1 | 5 | 1 | 2 | 2 | 4 | 0 | 2 |
| | 44 | 4 | 1 | 5 | 1 | 2 | 2 | 4 | 0 | 2 |
| | 45 | 4 | | | | | | | | |
| | 46 | 4 | 1 | 5 | 1 | 2 | 2 | 4 | 0 | 2 |
| | 47 | 4 | 0 | 5 | 1 | 2 | 2 | 4 | 0 | 1 |
| | 48 | 4 | 0 | 5 | 1 | 2 | 3 | 4 | 0 | 1 |
| | 49 | 4 | 0 | 5 | 1 | 2 | 3 | 4 | 0 | 1 |
| | 50 | 4 | 0 | 5 | 1 | 2 | 3 | 4 | 0 | 1 |
| | 51 | 4 | 0 | 5 | 1 | 2 | 3 | 4 | 0 | |
| | 52 | | | | | | | | | |
| | 53 | 4 | 0 | 5 | 1 | 2 | 3 | 4 | 0 | 1 |
| | 54 | 4 | 0 | 5 | 1 | 2 | 3 | 4 | 1 | 1 |
| | 55 | 4 | 0 | 5 | 1 | 2 | 3 | 4 | 1 | 1 |
| | 56 | 4 | 0 | 5 | 1 | 2 | 3 | 4 | 1 | 1 |
| | 57 | 4 | 0 | 5 | 1 | 2 | 3 | 4 | 1 | 1 |

In the group that was treated with 20 mg Copolymer 1, Female No. 285 showed a very acute onset of signs. On day 16, she reached score 2, and was euthanized two days later on day 18 (score 4). Female No. 793 had mild neurological symptoms (score 1) from day 54 until the end of follow up period. Female No. 494 showed mild signs from day 20 to 36, and reached score 2 from day 37 to 46, with an improvement (score 1) until the end of the follow up period.

A summary of the results is presented in Table 10 below.

TABLE 10

Evaluation of Clinical Manifestations

| Treatment Group | Incidence | Mean Score | Mean Maximal Score | Mean Disease Onset Day |
|---|---|---|---|---|
| Control | 3/3 | 2.9 ± 0.6 | 3.33 | 17 |
| 10 mg | 3/3 | 1.3 ± 0.56 | 2.33 | 30 |
| 20 mg | 3/3 | 1.6 ± 0.53 | 2.33 | 30 |

Figure 6:
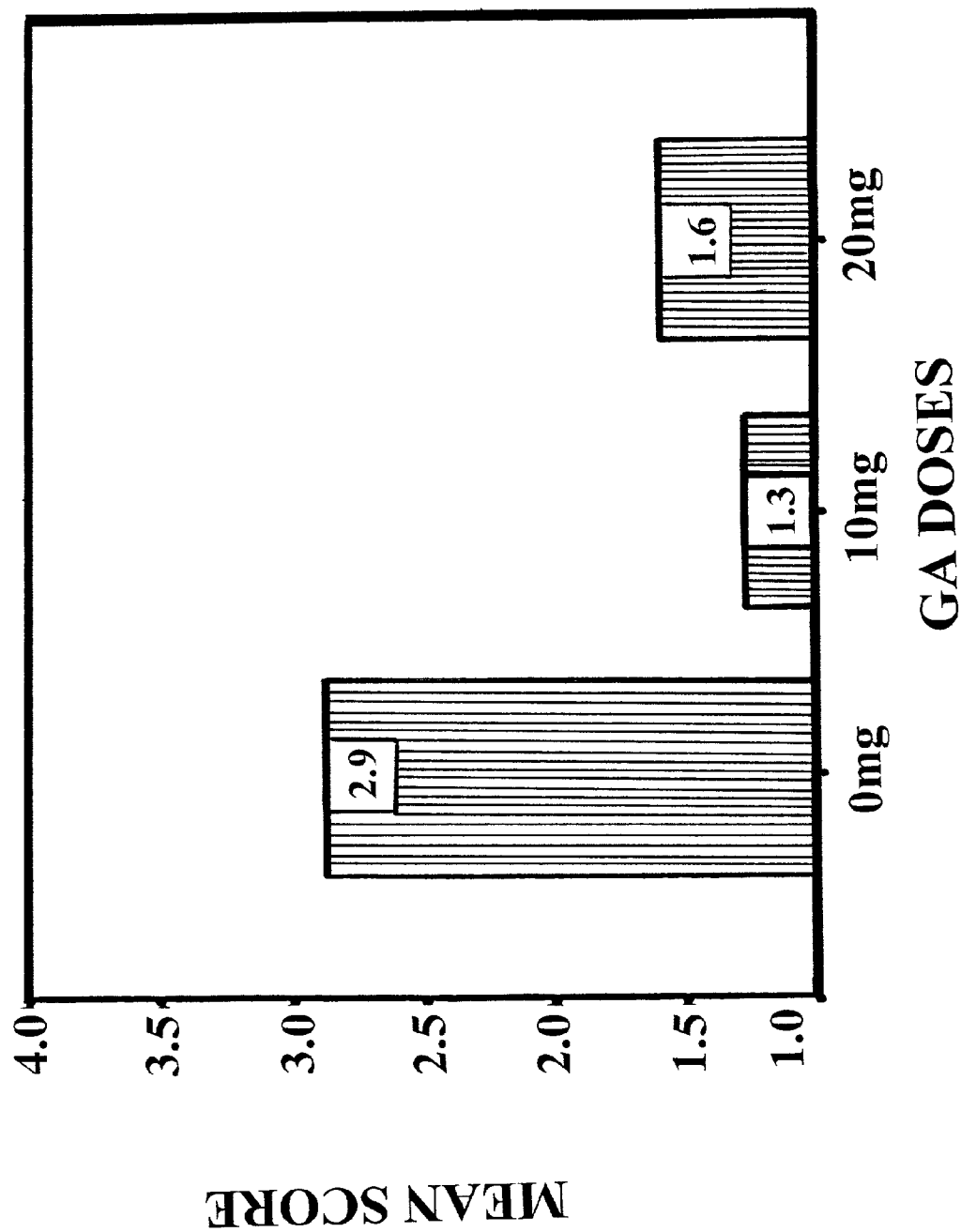
FIG. 6 shows the results of treatment of EAE treatment in Cynamologus monkeys by oral administration of Copolymer 1 in enteric-coated tablets.

A graphic summary appears in FIG. 6. Six females survived to the end of the follow up period and were sacrificed on day 57.

The phasic course of the disease was not clear as in Example 3B, with recurrence of symptoms and remission periods. Most of the animals developed acute or chronic disease. Acute onset of EAE appeared in the placebo group in two animals and in the 20 mg Copolymer 1 treatment group in one animal. In the group that was treated with 10 mg Copolymer 1, the pattern of disease was not as severe as in the other groups—all three animals developed chronic disease and survived through the whole study. The difference between the placebo group and the 10 mg Copolymer 1 group, and between the placebo group and the 20 mg Copolymer 1 group was statistically significant (p<0.0001). The difference is also significant between the 10 mg Copolymer 1 group and the 20 mg Copolymer 1 group (p<0.03). From evaluation of the clinical manifestations summarized in Table 10, it is evident that Copolymer 1 treatment does not change the incidence of the disease, but mainly affects the timing of the initial manifestation of the disease and the intensity of the symptoms. This data confirms the results of Example 3B, where the most effective dosage of Copolymer 1 was 10 mg.

Example 3D

Treatment of Relapsing—Remitting (RR) MS Patients With Copolymer 1 Enteric-Coated Tablets.

1,650 RR MS patients are recruited and randomized 1:1:1 into treatment with 5 mg Copolymer 1, 50 mg Copolymer 1 or placebo, in a framework of a phase III clinical trial. Patients are followed every 2 months for a total duration of 56 weeks.

The primary end point of the study is the reduction of relapse rate by the treatment with Copolymer 1 enteric-coated tablets. In the secondary outcome measures, the effect of Copolymer 1 on disease activity and burden of disease are monitored using magnetic resonance imaging (MRI).

In addition, the effect on brain atrophy, magnetization transfer (MT), spectroscopy (MRS) and disability are also being monitored, in order to demonstrate the effect of oral administration of Copolymer 1 in enteric-coated tablets on disease progression.

Discussion

When preparing oral formulations, characteristics such as desired site of action (e.g. gut), dosage amount, physical characteristics, and chemical characteristics, must be taken into consideration.

Copolymer 1 is a non-crystalline, highly porous, lyophilized material. It is only slightly soluble, and has poor mixing and very poor flow properties. In addition, Copolymer 1 is a proteinaceous material which is easily degraded by proteolytic enzymes in the gastrointestinal track. This disclosure provides Copolymer 1 formulations for oral administration which have pharmaceutical properties suitable for oral administration.

While microcrystalline cellulose has been used as a component in oral formulations, the formulations disclosed herein contain in excess of 50% by weight of microcrystalline cellulose. Such a composition, together with the disclosed milling/dry granulation manufacturing process results in oral formulations with excellent flow and mixing characteristics, improved dissolution and improved stability than that which could have been expected based on the properties of Copolymer 1.

Indeed, based on the properties of Copolymer 1, it was unexpected that formulation with microcrystalline cellulose, particularly in excess of 50%, would have significantly improved pharmaceutical properties suitable for oral administration.

The advantageous properties of the disclosed formulation include that it allows for matching in vitro dissolution profiles of the 5 mg Copolymer 1 and the 50 mg Copolymer 1 tablets, despite a 4-fold difference in tablet weight as shown in FIG. 3. Specifically, and unexpectedly, even thought the 50 mg Copolymer 1 tablet is four times the weight of the 5 mg Copolymer 1 tablet, the tablets have similar dissolution profiles.

What is claimed:

1. A pharmaceutical composition comprising as an active ingredient a therapeutically effective amount of glatiramer acetate, an amount of microcrystalline cellulose in excess of 50% by weight of the composition and an enteric coating.

2. The pharmaceutical composition of claim 1, further comprising a protease inhibitor.

3. The pharmaceutical composition of claim 1, wherein the amount of microcrystalline cellulose is from about 60% to about 90% by weight.

4. The pharmaceutical composition of claim 1, wherein the amount of microcrystalline cellulose is from about 70% to about 80% by weight.

5. The pharmaceutical composition of claim 1, wherein the microcrystalline cellulose has a moisture content of up to 5.0%.

6. The pharmaceutical composition of claim 1, wherein the microcrystalline cellulose has a moisture content of up to 1.5%.

7. The pharmaceutical composition of claim 1, further comprising a disintegrant.

8. The pharmaceutical composition of claim 7, wherein the disintegrant is selected from the group consisting of kaolin, starch, powdered sugar, sodium starch glycolate, crosscarmelose sodium, carboxymethyl cellulose, microcrystalline cellulose and sodium alginate.

9. The pharmaceutical composition of claim 8, wherein the disintegrant is a pregelatinized starch.

10. The pharmaceutical composition of claim 9, wherein the starch has a moisture content of up to 14%.

11. The pharmaceutical composition of claim 9, wherein the starch has a moisture content of up to 12%.

12. The pharmaceutical composition of claim 9, wherein the starch has a moisture content of up to 7%.

13. The pharmaceutical composition of claim 9, wherein the starch has a moisture content of up to 5%.

14. The pharmaceutical composition of claim 1, further comprising a lubricant.

15. The pharmaceutical composition of claim 14, wherein the lubricant is selected from the group consisting of talc, sodium stearyl fumarate, magnesium stearate, calcium stearate, hydrogenated castor oil, hydrogenated soybean oil, and polyethylene glycol.

16. The pharmaceutical composition of claim 15, wherein the lubricant is magnesium stearate.

17. The pharmaceutical composition of claim 1, wherein the enteric coating is methacrylic acid copolymer.

18. The pharmaceutical composition of claim 1, wherein the enteric coating is selected from the group consisting of cellulose acetate phthalate (CAP), hydroxypropyl methyl cellulose phthalate (HPMCP), carboxymethyl ethyl cellulose (CMEC), or amino-alkylmethacrylate copolymer.

19. The pharmaceutical compositionof claim 1, further comprising a film coating under the enteric coating.

20. The pharmaceutical composition of claim 19, wherein the film coating is selected from the group consisting of hydroxy propyl methyl cellulose (HPMC) and poly vinyl alcohol (PVA).

21. The pharmaceutical composition of claim 1 in solid form.

22. The pharmaceutical composition of claim 21, wherein the solid form is selected from the group consisting of a tablet, a hard gelatin capsule, a pellet and a particulate formulation.

23. The pharmaceutical composition of claim 22, wherein the solid form is a tablet and the effective amount of glatiramer acetate is from about 0.1 mg to about 300 mg.

24. The pharmaceutical composition of claim 23, wherein the effective amount of glatiramer acetate is from about 5 mg to about 100 mg.

25. The pharmaceutical composition of claim 23, wherein the effective amount of glatiramer acetate is about 5 mg.

26. The pharmaceutical composition of claim 23, wherein the effective amount of glatiramer acetate is about 50 mg.

27. The pharmaceutical composition of claim 1, further comprising a pharmaceutically acceptable carrier suitable for application to mucosal linings, so as to thereby form a composition suitable for application to the mucosal linings of a subject.

28. The pharmaceutical composition of claim 27, wherein the carrier is chitosan.

29. The pharmaceutical composition of claim 28, further comprising a pharmaceutically effective amount of an anti-microbial preservative.

30. The pharmaceutical composition of claim 29, wherein the anti-microbial preservative is selected from the group consisting of sodium benzoate, methyl paraben, benzalkonium chloride, and propyl paraben.

31. The pharmaceutical composition of claim 27, in dry powder form.

32. The pharmaceutical composition of claim 27, wherein the mucosal linings are bronchi-associated lymphoid tissue.

33. The pharmaceutical composition of claim 27, formulated for oral administration.

34. The pharmaceutical composition of claim 27, formulated for nasal administration.

35. The pharmaceutical composition of claim 27, formulated for pulmonary administration.

36. The pharmaceutical composition of claim 27, formulated for buccal administration.

37. The pharmaceutical composition of claim 1, wherein the amount of microcrystalline cellulose is at least 70% by weight.

38. The pharmaceutical composition of claim 31 in solid form.

39. The pharmaceutical composition of claim 38, wherein the solid form is selected from the group consisting of a tablet, a hard gelatin capsule, a pellet and a particulate formulation.

40. The pharmaceutical composition of claim 39, wherein the effective amount of glatiramer acetate is about 5 mg.

41. The pharmaceutical composition of claim 39, wherein the effective amount of glatiramer acetate is about 50 mg.

42. A process for manufacturing the composition of claim 1, comprising:
  a) milling the glatiramer acetate
  b) dry mixing the milled glatiramer acetate with at least 50% by weight of microcrystalline cellulose.

43. The process of claim 42, further comprising applying a film coating.

44. The process of claim 42, further comprising applying an enteric coating.

45. The process of claim 42, wherein the enteric coating is applied using a rotating pan system.

46. A pharmaceutical composition in solid form comprising as an active ingredient a therapeutically effective amount of glatiramer acetate, 70%–80% by weight of microcrystalline cellulose, and an enteric coating.

47. The pharmaceutical composition of claim 46, wherein the effective amount of glatiramer acetate is from about 5 mg to about 100 mg.

48. The pharmaceutical composition of claim 46, wherein the effective amount of glatiramer acetate is about 5 mg.

49. The pharmaceutical composition of claim 46, wherein the effective amount of glatiramer acetate is about 50 mg.

50. The pharmaceutical composition of claim 46, wherein the effective amount of glatiramer acetate is from about 0.01 mg/kg to about 2 mg/kg.

51. The pharmaceutical composition of claim 46, wherein the effective amount of glatiramer acetate is from about 0.05 mg/kg to about 1 mg/kg.

* * * * *